(12) United States Patent
Gelb et al.

(10) Patent No.: US 8,088,745 B2
(45) Date of Patent: Jan. 3, 2012

(54) METHODS FOR ASSAYING ALPHA-L-IDURONIDASE ENZYMATIC ACTIVITY

(75) Inventors: Michael H. Gelb, Seattle, WA (US); Sophie Blanchard, Seattle, WA (US)

(73) Assignee: University of Washington, Seattle, WA (US)

( * ) Notice: Subject to any disclaimer, the term of this patent is extended or adjusted under 35 U.S.C. 154(b) by 65 days.

(21) Appl. No.: 12/706,794

(22) Filed: Feb. 17, 2010

(65) Prior Publication Data

US 2010/0209951 A1 Aug. 19, 2010

Related U.S. Application Data

(63) Continuation of application No. PCT/US2008/073516, filed on Aug. 18, 2008.

(60) Provisional application No. 60/956,644, filed on Aug. 17, 2007.

(51) Int. Cl.
*A61K 31/7034* (2006.01)
*A61K 31/7028* (2006.01)
*C07H 17/075* (2006.01)
*C07H 15/20* (2006.01)

(52) U.S. Cl. .............................. 514/27; 514/28; 536/17.9

(58) Field of Classification Search ........................ None
See application file for complete search history.

(56) References Cited

U.S. PATENT DOCUMENTS 5,773,236 A 6/1998 Diwu
6,670,194 B1 12/2003 Aebersold

FOREIGN PATENT DOCUMENTS

WO 93/04192 A1 3/1993
WO 99/46402 A2 9/1999
WO 2006/102958 A1 10/2006

OTHER PUBLICATIONS

Chamoles, N.A., et al., "Diagnosis of α-L-Iduronidase Deficiency in Dried Blood Spots on Filter Paper: The Possibility of Newborn Diagnosis," Clinical Chemistry 47(4):780-781, Apr. 2001.

Li, Y., et al., "Tandem Mass Spectrometry for the Direct Assay of Enzymes in Dried Blood Spots: Application to Newborn Screening for Krabbe Disease," Clinical Chemistry 50(3):638-640, Mar. 2004.

Li, Y., et al., "Direct Multiplex Assay of Lysosomal Enzymes in Dried Blood Spots for Newborn Screening," Clinical Chemistry 50(10):1785-1796, Oct. 2004.

Wang, D., et al., "Tandem Mass Spectrometric Analysis of Dried Blood Spots for Screening of Mucopolysaccharidosis I in Newborns," Clinical Chemistry 51(5):898-900, May 2005.

Wang, D., et al., "Tandem Mass Spectrometry for the Direct Assay of Enzymes in Dried Blood Spots: Application to Newborn Screening for Mucopolysaccharidosis II (Hunter Disease)," Clinical Chemistry 53(1):137-140, Jan. 2007.

Hopwood, J.J., et al., "A Fluorometric Assay Using 4-Methylumbelliferyl-α-L-Iduronide for the Estimation of α-L-Idurodinase Activity and the Detection of Hurler and Scheie Syndromes," Clinica Chimica Act 92(2):257-265, Mar. 1979.

Mandelli, J., et al., "Detection of Mucopolysaccharidosis Type I Heterozygotes Based on the Biochemical Characteristics of Leukocyte α-L-Iduronidase," Archives of Medical Research 33(1):20-24, Jan. 2002.

International Search Report and Written Opinion of the International Searching Authority, mailed Feb. 2, 2009, in corresponding International Application No. PCT/US2008/073516, filed Aug. 18, 2008, 11 pages.

*Primary Examiner* — Eric S Olson

(74) *Attorney, Agent, or Firm* — Christensen O'Connor Johnson Kindness PLLC

(57) ABSTRACT

Methods for assaying α-L-iduronidase enzymatic activity and methods for screening newborns for Mucopolysaccharidosis Type-I.

16 Claims, 11 Drawing Sheets

IdA-IS (*m/z* 377.2 for M+H⁺)   Fragment derived from IdA-IS (*m/z* 277.1 for M+H⁺)

METHODS FOR ASSAYING ALPHA-L-IDURONIDASE ENZYMATIC ACTIVITY

CROSS-REFERENCE TO RELATED APPLICATION

This application is a continuation of International Application No. PCT/US2008/073516, filed Aug. 18, 2008, which claims the benefit of U.S. Provisional Application No. 60/956,644, filed Aug. 17, 2007. Each application is expressly incorporated herein by reference in its entirety.

STATEMENT OF GOVERNMENT LICENSE RIGHTS

This invention was made with Government support under Government Contract No. 2RO1DK067859-07 awarded by the National Institutes of Health. The Government has certain rights in the invention.

BACKGROUND OF THE INVENTION

Newborn screening programs have been established to quantify the level of metabolites associated with treatable diseases. Mucopolysaccharidosis type I (MPS-I) is a lysosomal storage disorder caused by the deficiency of α-L-iduronidase (IdA; EC 3.2.1.76) enzymatic activity and can manifest three major clinical phenotypes: Hurler, Scheie, and Hurler-Scheie syndromes.

IdA is essential for the degradation of the glycosaminoglycans dermatan and heparan sulfate within lysosomes. Failure to breakdown these polysaccharides causes physical changes such as joint stiffness, skeletal abnormalities, and corneal clouding. Hurler syndrome is characterized by valvular heart disease, mental deterioration, and death in childhood. As symptoms may not be recognized early in life, the diagnosis of MPS-I is a challenging task. Enzyme replacement therapy and bone marrow transplantation have been developed for this disease, and both are beneficial if performed early. Because early detection is necessary for optimum clinical response to therapy, the need for developing screens for the early recognition of MPS-I is of great interest.

Tandem mass spectrometry (tandem MS or MSMS) is one platform for measuring disease-associated enzyme activities using rehydrated dried blood spots (DBS) for the quantitative measurement of the activities of enzymes responsible for several lysosomal storage disorders. In addition to electrospray ionization tandem mass spectrometry (ESI-MSMS) assays, fluorometric and radiometric assays for α-L-iduronidase have been developed.

Treatments now available for MPS-I require early detection for optimum clinical response to therapy. Accordingly, there exists a need for methods for newborn screening of the activity of the relevant enzyme, α-L-iduronidase. The present invention fulfills this need and provides further related advantages.

SUMMARY OF THE INVENTION

In one aspect, the invention provide methods for assaying α-L-iduronidase enzymatic activity.

In one embodiment, the method includes extracting an aqueous enzyme reaction mixture comprising α-L-iduronidase, an α-L-iduronidase product, and an α-L-iduronidase internal standard with an organic solvent to provide an organic phase comprising the α-L-iduronidase product and α-L-iduronidase internal standard; and determining the quantity of the α-L-iduronidase product.

In another embodiment, the invention provides a method for assaying α-L-iduronidase enzymatic activity, comprising:

(a) incubating an α-L-iduronidase substrate with α-L-iduronidase for a pre-determined time to provide a solution comprising an α-L-iduronidase product;

(b) adding a buffer to the solution comprising the α-L-iduronidase product to quench the enzyme reaction;

(c) adding an α-L-iduronidase internal standard to the solution comprising the α-L-iduronidase product to provide a solution comprising the α-L-iduronidase product and α-L-iduronidase internal standard;

(d) extracting the solution comprising the α-L-iduronidase product and α-L-iduronidase internal standard with an organic solvent to provide an organic phase that includes the α-L-iduronidase product and α-L-iduronidase internal standard; and (e) determining the quantity of the α-L-iduronidase product.

In one embodiment, the solution comprising α-L-iduronidase is obtained by contacting a sample containing α-L-iduronidase with a first buffer solution. In one embodiment, the sample is a blood sample. In one embodiment, the sample is a dried blood spot from a newborn screening card.

In one embodiment, the substrate has formula (I):

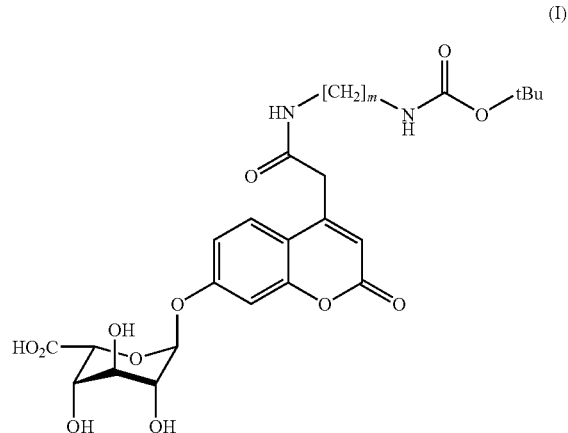

wherein m is an integer from 2 to 12. In one embodiment, the substrate is (N-[4"-(tert-butoxycarbonylamino)-butyl]) 7-O-(α-L-idopyranosyluronic acid)coumarin-4-acetamide.

In one embodiment, the internal standard has formula (II):

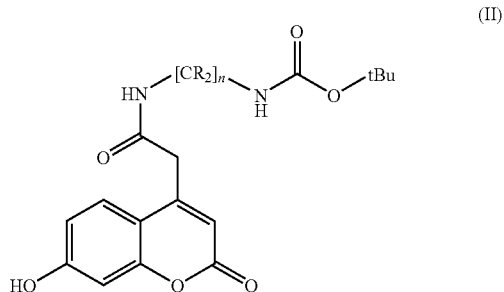

wherein R is independently at each occurrence H or D and n is an integer from 2 to 12. In one embodiment, the internal standard is (N-[3'-(tert-butoxycarbonylamino)-propyl]) 7-hydroxycoumarin-4-acetamide.

In one embodiment, the organic solvent is ethyl acetate.

In one embodiment, determining the quantity of the α-L-iduronidase product comprises determining the ratio of the α-L-iduronidase product to α-L-iduronidase internal standard comprises mass spectrometric analysis. In one embodiment, determining the quantity of the α-L-iduronidase product comprises tandem mass spectrometric analysis. In one embodiment, determining the quantity of the α-L-iduronidase product comprises tandem mass spectrometric analysis in which the parent ions of the product and internal standard are generated, isolated, and subjected to collision-induced dissociation to provide product fragment ions and internal standard fragment ions. In one embodiment, determining the quantity of the α-L-iduronidase product comprises comparing the peak intensities of the product fragment ions and internal standard fragment ions to calculate the amount of α-L-iduronidase product.

In one embodiment, the method further includes the step of using the amount of α-L-iduronidase product to determine whether the dried blood sample is from a candidate for treatment for Mucopolysaccharidosis Type-I.

Other embodiments of the method of the invention include:
a method for assaying α-L-iduronidase enzymatic activity, comprising
(a) incubating an α-L-iduronidase substrate with α-L-iduronidase to provide an enzyme reaction mixture containing an α-L-iduronidase product,
(b) quenching the enzyme reaction with a buffer solution comprising an α-L-iduronidase internal standard,
(c) extracting the enzyme reaction mixture with an organic solvent to provide an organic phase comprising the α-L-iduronidase product and α-L-iduronidase internal standard, and
(d) determining the quantity of the α-L-iduronidase product; and
a method for assaying α-L-iduronidase enzymatic activity, comprising
(a) incubating an α-L-iduronidase substrate with α-L-iduronidase in the presence of an α-L-iduronidase internal standard to provide an enzyme reaction mixture containing an α-L-iduronidase product,
(b) quenching the enzyme reaction,
(c) extracting the enzyme reaction mixture with an organic solvent to provide an organic phase comprising the α-L-iduronidase product and α-L-iduronidase internal standard, and
(d) determining the quantity of the α-L-iduronidase product.

In another aspect of the invention, a method for screening newborns for Mucopolysaccharidosis Type-I is provided. In one embodiment, the method includes:
(a) contacting a dried blood sample from a newborn screening card with a first buffer solution to provide a solution comprising α-L-iduronidase;
(b) adding an α-L-iduronidase substrate to the solution comprising α-L-iduronidase and incubating the substrate with the enzyme for a pre-determined time to provide a solution comprising an α-L-iduronidase product;
(c) adding a second buffer to the solution comprising the α-L-iduronidase product to quench the enzyme reaction;
(d) adding an α-L-iduronidase internal standard to the solution comprising the α-L-iduronidase product to provide a solution comprising the α-L-iduronidase product and α-L-iduronidase internal standard;

(e) extracting the solution comprising the α-L-iduronidase product and α-L-iduronidase internal standard with an organic solvent to provide an organic phase that includes the α-L-iduronidase product and α-L-iduronidase internal standard;
(f) determining the quantity of the α-L-iduronidase product by tandem mass spectrometric analysis, comprising
(i) generating, isolating, and subjecting the parent ions of the product and internal standard to collision-induced dissociation to provide product fragment ions and internal standard fragment ions, and
(ii) comparing the ion peak intensities of the product fragment ions and internal standard fragment ions to calculate the amount of α-L-iduronidase product; and
(g) using the amount of α-L-iduronidase product to predict whether the newborn is a candidate for treatment of Mucopolysaccharidosis Type-I.

In another aspect, the invention provides compounds having formula (I):

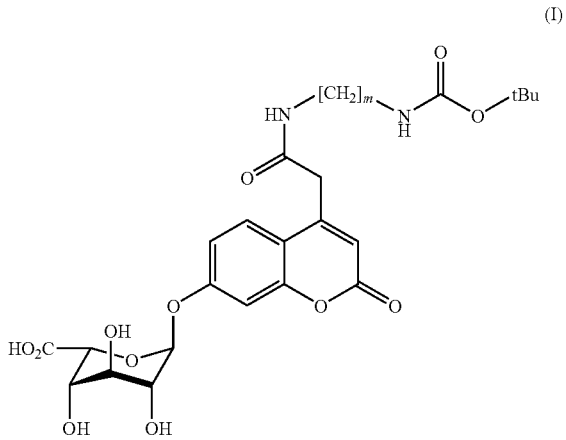

(I)

wherein m is an integer from 2 to 12. In one embodiment, the compound is (N-[4"-(tert-butoxycarbonylamino)-butyl]) 7-O-(α-L-idopyranosyluronic acid)coumarin-4-acetamide. The compounds are useful in the methods of the invention as substrates for α-L-iduronidase.

In another aspect, the invention provides compounds having formula (II):

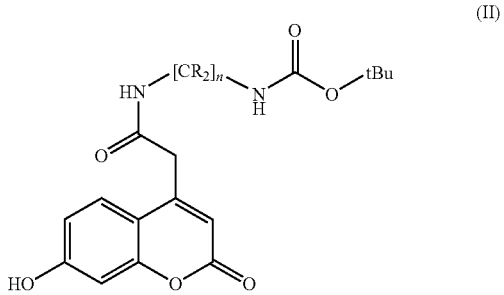

(II)

wherein R is independently at each occurrence H or D and n is an integer from 2 to 12. In one embodiment, the compound is (N-[3'-(tert-butoxycarbonylamino)-propyl]) 7-hydroxycoumarin-4-acetamide. The compounds are useful in the methods of the invention as internal standards.

In another aspect, the invention provides a fluorometric method for assaying α-L-iduronidase enzymatic activity, comprising:

(a) contacting a dried blood sample with a first buffer solution to provide a solution comprising α-L-iduronidase;

(b) adding an α-L-iduronidase substrate to the solution comprising α-L-iduronidase and incubating the substrate with the enzyme for a pre-determined time to provide a solution comprising an α-L-iduronidase product;

(c) adding a second buffer to the solution to quench the enzyme reaction;

(d) separating the α-L-iduronidase product from the enzyme reaction; and (e) measuring the fluorescence intensity of a solution containing the α-L-iduronidase product.

In one embodiment, the fluorometric method includes a liquid-liquid extraction step to separate the α-L-iduronidase product from the enzyme reaction mixture. In another embodiment, the fluorometric method includes a solid phase extraction step to separate the α-L-iduronidase product from the enzyme reaction mixture. In one embodiment, the α-L-iduronidase substrate is a compound of formula (I).

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
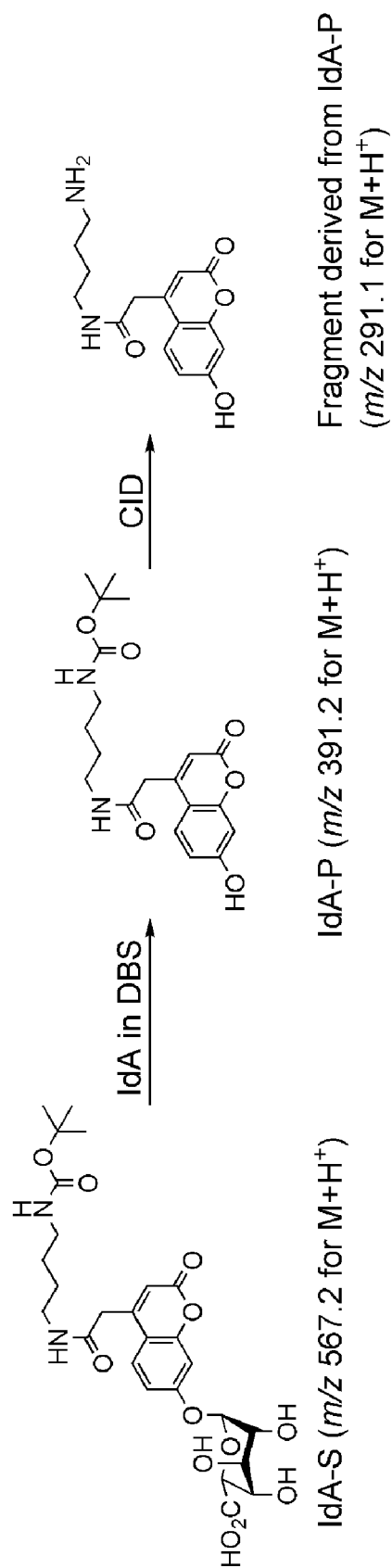
FIG. 1 illustrates a representative iduronidase substrate (IdA-S), its corresponding enzyme product (IdA-P), and the fragment derived from the enzyme product resulting from collision-induced dissociation (CID) analyzed by a method of the invention.

In one aspect, the present invention provides methods for assaying α-L-iduronidase enzymatic activity. In embodiments of the methods, the quantity of an α-L-iduronidase product is determined by comparing a signal derived from the enzyme product to signal derived from a known quantity of an α-L-iduronidase internal standard. The amount of the α-L-iduronidase product is determined by the enzymatic activity of α-L-iduronidase on an α-L-iduronidase substrate that is added to the sample to be assayed and the quantification of the enzyme product provides the measure of the α-L-iduronidase enzymatic activity in the sample. The methods are useful for assaying α-L-iduronidase enzymatic activity in newborns to evaluate whether the newborn suffers from a deficiency of α-L-iduronidase enzymatic activity and is therefore a candidate for treatment for Mucopolysaccharidosis Type-I.

In one embodiment of the method, the α-L-iduronidase product and the α-L-iduronidase internal standard differ in mass and the quantity of α-L-iduronidase product is determined by mass spectrometry.

In certain embodiments of the methods, the α-L-iduronidase product and α-L-iduronidase internal standard are extracted from the aqueous enzyme reaction mixture containing α-L-iduronidase, excess α-L-iduronidase substrate, the α-L-iduronidase product, and α-L-iduronidase internal standard by liquid-liquid extraction using an organic solvent.

In other embodiments, the aqueous enzyme reaction mixture noted above is applied to a suitable solid phase from which the α-L-iduronidase product and α-L-iduronidase internal standard are eluted.

In each method, quantification of the α-L-iduronidase product is facilitated by quantifying the α-L-iduronidase internal standard.

In one embodiment, the method for assaying α-L-iduronidase enzymatic activity, includes the following steps:

(a) contacting a dried blood sample with a first buffer solution to provide a solution comprising α-L-iduronidase;

(b) adding an α-L-iduronidase substrate to the solution comprising α-L-iduronidase and incubating the substrate with the enzyme for a pre-determined time to provide a solution comprising an α-L-iduronidase product;

(c) adding a second buffer to the solution comprising the α-L-iduronidase product to quench the enzyme reaction;

(d) adding an α-L-iduronidase internal standard to the solution comprising the α-L-iduronidase product to provide a solution comprising the α-L-iduronidase product and α-L-iduronidase internal standard;

(e) extracting the solution comprising the α-L-iduronidase product and α-L-iduronidase internal standard with an organic solvent to provide an organic phase that includes the α-L-iduronidase product and α-L-iduronidase internal standard;

(f) determining the quantity the α-L-iduronidase product.

In one embodiment, the dried blood sample is a dried blood spot from a newborn screening card. However, the method can be performed on any sample that contains α-L-iduronidase including specimens (e.g., plasma, serum, tissue) from human, animal, and non-living sources. Blood samples other than dried blood are also suitable for assay by the method.

In the method, a sample containing α-L-iduronidase is contacted with a first buffer solution to provide a solution comprising α-L-iduronidase. The step can be considered to be an extraction step in which α-L-iduronidase in the sample (e.g., dried blood spot) is extracted into an aqueous liquid phase so that enzymatic reaction can occur. The solution need not be homogeneous and need only provide an aqueous liquid phase sufficient for enzymatic reaction between α-L-iduronidase and the α-L-iduronidase substrate. In one embodiment, the first buffer is an aqueous buffer having pH about 3.4 (e.g., 0.1 mol/L sodium formate containing 75 μmol/L D-saccharic acid 1,4-lactone). The first buffer has pH sufficient to extract and dissolve the enzyme from the sample, as necessary, to provide an enzyme reaction mixture that provides an enzyme product by incubation of the enzyme with a substrate. Suitable buffers have a pH from about 2.8 to 4.2. It will be appreciated that in certain embodiments, the sample can be added directly to an assay buffer that includes an α-L-iduronidase substrate.

To assay α-L-iduronidase enzymatic activity, an α-L-iduronidase substrate is incubated with the α-L-iduronidase to provide an α-L-iduronidase product. In one embodiment, the α-L-iduronidase substrate is added to the α-L-iduronidase solution and incubated for a pre-determined time to provide a solution comprising an α-L-iduronidase product. The pre-determined time can vary and will depend on the amount of enzymatic activity of the sample and the sensitivity of the analytical method for quantifying the enzyme product and internal standard. In one embodiment, incubating for a pre-determined time includes incubating the substrate with the enzyme at 37° C. for 20 hours. Pre-determined incubation times can range from less than one hour to more than 20 hours depending on the sample. In one embodiment, the substrate is included in the assay buffer solution (i.e., the first buffer solution). After the pre-determined time, the enzyme reaction is quenched (i.e., stopped) by the addition of a second buffer (e.g., 0.1 mol/L sodium acetate pH 5.4). The quenching buffer has a pH sufficient to stop the enzyme reaction. The pH of the enzyme reaction mixture is such that separation of the enzyme product and internal standard is achieved without significant amounts of substrate also being extracted (i.e., pH≧pKa of substrate carboxylic acid group).

In certain embodiments of the invention, the quantity of enzyme product is determined by comparing the signal associated with the α-L-iduronidase internal standard to the signal associated with the α-L-iduronidase product. In one embodiment of the method, the internal standard is added to the quenched enzyme reaction mixture that includes the α-L-iduronidase product. Alternatively, the α-L-iduronidase internal standard can be added as a component of the second buffer used to quench the enzyme reaction, or the internal standard can be added with the substrate prior to incubation with the enzyme.

In the methods, the α-L-iduronidase product and α-L-iduronidase internal standard are separated from the aqueous enzyme reaction mixture (i.e., separated from the enzyme and excess substrate) for further analysis. In one embodiment, the aqueous enzyme reaction mixture is extracted with an organic solvent to provide an organic phase that includes the enzyme product and internal standard. Suitable organic solvents are substantially immiscible with water and are not effective in solubilizing the enzyme or enzyme substrate. Suitable organic solvents selectively and efficiently extract the product and internal standard, and extract each substantially equally (i.e., the enzyme product and internal standard have substantially the same partition coefficients for a given solvent). Suitable solvents include ethyl acetate, diethyl ether, chloroform, methylene chloride, and butanol. In one embodiment, the organic solvent is ethyl acetate.

In another embodiment, the enzyme product is separated from the aqueous enzyme reaction mixture (including internal standard) by solid phase extraction. In this embodiment of the method of the invention, the enzyme substrate is a compound having formula (I) and the internal standard is a compound having formula (II). In this embodiment, the aqueous enzyme reaction mixture is applied to a suitable solid phase. Suitable solid phases are effective in selectively retaining and releasing the enzyme product and internal standard substantially equally. Representative solid phases include silica gel, reverse-phase silica (e.g., C18-silica), and ion exchange resins, such as anion exchange resins. The enzyme product and internal standard can then be eluted from the solid phase, either sequentially or simultaneously, with one or more suitable organic solvents and the resulting solution(s) analyzed as described herein. Suitable organic solvents elute the enzyme product and internal standard substantially completely from the solid phase. The product and internal standard can be eluted from the solid phase either separately or together. In one embodiment, the product and internal standard are eluted together.

Once the enzyme product and internal substrate have been isolated, the enzyme product is quantitated. In certain embodiments of the methods, the determination of the quantity of enzyme product is facilitated by the internal standard. Because the quantity of the internal standard is known, measuring a signal associated with the internal standard and comparing that signal to the signal associated with the enzyme product allows for the determination of the quantity of enzyme product. As noted above, the signal associated with the enzyme product and internal standard can be measured by mass spectrometry (e.g., tandem mass spectrometry).

In one embodiment, the quantity of enzyme product is determined by determining the ratio of the α-L-iduronidase product to α-L-iduronidase internal standard by tandem mass spectrometric analysis. In the MSMS method, parent ions of the product and internal standard are generated, isolated, and subjected to collision-induced dissociation to provide product fragment ions and internal standard fragment ions, respectively. Comparing the peak intensities of the product fragment ions and internal standard fragment ions allows for the calculation the amount of α-L-iduronidase product.

In the methods of the invention, a known amount of α-L-iduronidase internal standard is added as described above to the enzymatic reaction system, which ultimately generates the α-L-iduronidase product in the presence of α-L-iduronidase. In the tandem mass spectrometric methods of the invention, the peak area integrals for the enzyme product fragment ion and the internal standard fragment ion are measured and the ratio of the enzyme product peak area to the internal standard peak area is multiplied by the number of moles of internal standard added to provide the number of moles of enzyme product, thereby quantitating the enzyme product produced by α-L-iduronidase in the original sample.

The tandem mass spectrometric methods of the invention effectively quantify the α-L-iduronidase product. The methods are effectively when the parent mass of the product and internal standard are the same and their fragments are different, or the parent mass of the product and internal standard are different and the fragments are both the same or are both different.

The methods of the invention for assaying α-L-iduronidase enzymatic activity depend on the measurement of signals from the α-L-iduronidase product and α-L-iduronidase internal standard. The enzyme product and internal standard are related in several ways. For the methods of the invention that rely on liquid-liquid extraction for isolation of the enzyme product from the aqueous enzyme reaction mixture, each is extractable into the organic extraction solvent substantially equally (ideally the same). For the methods of the invention that rely on mass spectrometric analysis, each produces a fragment ion having a mass that is different and that can be resolved from the other, and the product and internal fragment ions are produced from respective fragments having substantially the same ionization efficiency (ideally the same).

Representative enzyme substrates have formula (I):

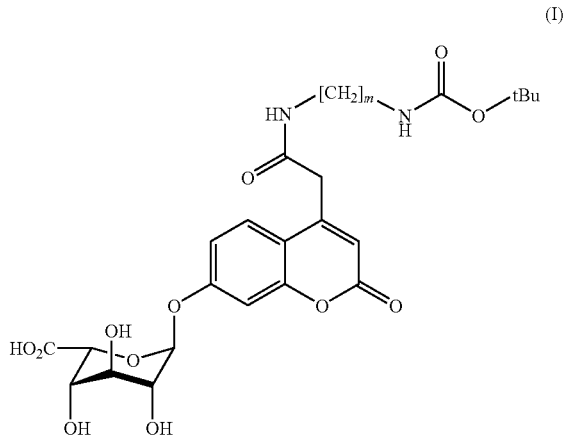

(I)

wherein m is an integer from 1 to 20. In one embodiment, m is from 2-12. In one embodiment, m is 4 (i.e., N-[4"-(tert-butoxycarbonylamino)-butyl]) 7-O-(α-L-idopyranosyluronic acid)coumarin-4-acetamide).

Representative internal standards have formula (II):

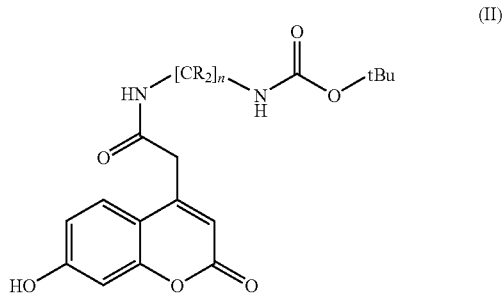

(II)

wherein R is independently at each occurrence H or D and n is an integer from 1 to 20. In one embodiment, m is from 2-12.

In one embodiment, R is H and n is 3 (i.e., (N-[3'-(tert-butoxycarbonylamino)-propyl]) 7-hydroxycoumarin-4-acetamide).

In the methods of the invention, the enzyme substrate (e.g., compounds of formula (I)) and the internal standard (e.g., compounds of formula (II)) are related. For example in the representative method of the invention described in Example 3, the enzyme substrate is a compound of formula (I) with m=4 and the internal standard is a compound of formula (II) with m=3. For this pair of substrate and internal standard, the enzyme product and internal standard differ by a single methylene unit. Mass spectrometric analysis readily distinguishes fragment ions from each and allows for their quantitation. For methods of the invention that employ mass spectrometric analysis, enzyme substrates and internal standards are selected from the compounds of formulas (I) and (II), respectively, such that when R is H for formula (II), m≠n (i.e., the substrate and standard differ by at least one methylene unit).

Alternatively, for methods of the invention that employ mass spectrometric analysis, enzyme substrates and internal standards can be selected from the compounds of formulas (I) and (II), respectively, where m=n, when the internal standard includes one or more heavy atoms (e.g., not every R in the methylene chain is hydrogen).

A representative α-L-iduronidase product (IdA-P) useful in the methods of the invention is illustrated in FIG. 1. The α-L-iduronidase substrate (IdA-S) that produces the enzyme product is also illustrated in FIG. 1. IdA-S was prepared from inexpensive starting materials in thirteen (13) steps. The substrate is an umbelliferyl-α-L-iduronide to which is attached a four-carbon chain terminated by a t-butyl carbamylated amino group. Incubation with IdA present in DBS leads to enzymatic release of the iduronyl group to produce the umbelliferyl derivative product IdA-P (see FIG. 1).

Figure 2:
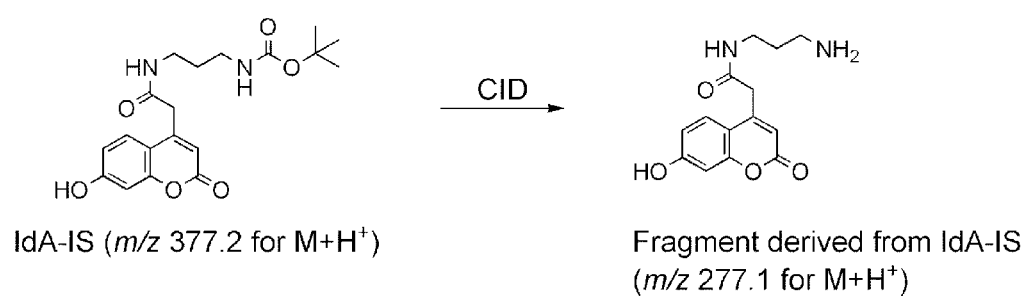
FIG. 2 illustrates a representative iduronidase internal standard (IdA-IS) and the fragment derived from the internal standard resulting from collision-induced dissociation (CID) analyzed by a method of the invention.

A representative α-L-iduronidase internal standard (IdA-IS) useful in the methods of the invention is illustrated in FIG. 2. IdA-IS is closely related to IdA-P, and in this embodiment, its carbon chain is shorter by one methylene group so that the internal standard has a different molecular weight (see FIG. 2). IdA-P and IdA-IS are separately detected and quantified by ESI-MSMS as their fragment ions, after collision-induced elimination of the t-butylcarbamate group (100-Da mass difference; see FIGS. 1 and 2). In a representative method, ESI-MSMS was carried out on a tandem quadrupole instrument operating in positive-ion, multiple-reaction monitoring mode. The parent ions for IdA-P and IdA-IS (m/z 391.2 and 377.2, respectively) were isolated and subjected to collision-induced dissociation (CID). The fragment ions analyzed are m/z 291.1 and 277.1 derived from IdA-P and IdA-IS, respectively, by elimination of isobutene and carbon dioxide. The amount of product was calculated by comparing the ion peak intensities of IdA-P with IdA-IS.

Figure 3:
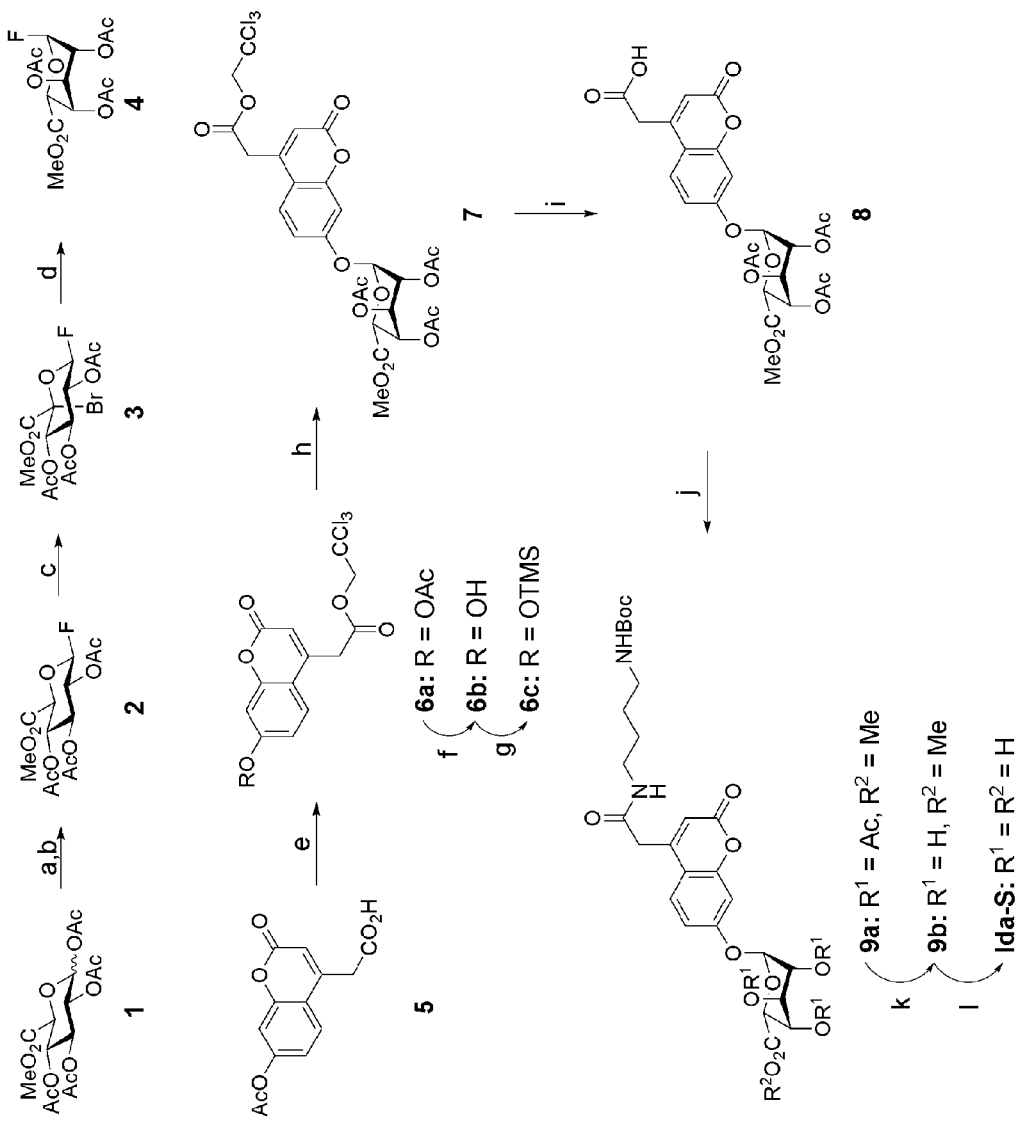
FIG. 3 is a schematic illustration of the synthesis of a representative iduronidase substrate (IdA-S) useful in the method of the invention; reagents and conditions: (a) HBr/AcOH; (b) AgF, MeCN, 74% (2 steps); (c) NBS, $CCl_4$, hv, reflux, 77%; (d) $Bu_3SnH$, benzene, reflux, 65%; (e) $HOCH_2CCl_3$, DCC, $CH_2Cl_2$, 96%; (f) 2 M $NH_3$ in 2-propanol, THF, 78%; (g) $(Me_3Si)_2NH$, $LiClO_4/SiO_2$, $CH_2Cl_2$; (h) i. Compound 4, $BF_3.OEt_2$, $CH_2Cl_2$; ii. $BF_3.OEt_2$, $Ac_2O$, 88% (2 steps); (i) Zn dust, $CuCl_2$, 90% aq. AcOH, THF, 0° C., 95%; (j) $H_2N(CH_2)_4NHBoc$, EDC, HOBt, THF, 65%; (k) NaOMe, MeOH, 86%; (l) NaOH, $MeOH/H_2O$ (1:1), quant.
Figure 4:
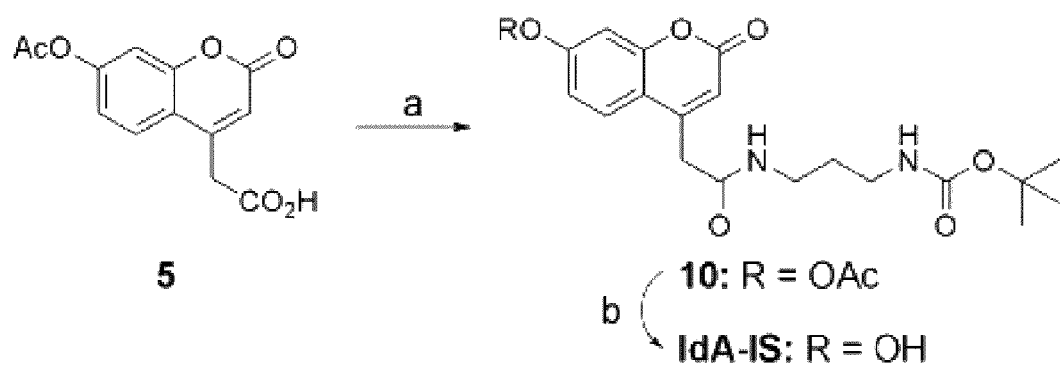
FIG. 4 is a schematic illustration of the synthesis of a representative iduronidase internal standard (IdA-IS) useful in the method of the invention; reagents and conditions: (a) $H_2N(CH_2)_3NHBoc$, EDC, HOBt, THF, 61%; (b) NaOMe, $MeOH/CH_2Cl_2$ (6:1), 92%.

The syntheses of the representative enzyme substrate and internal standard noted above are described in Examples 1 and 2 and illustrated schematically in FIGS. 3 and 4, respectively.

In the methods of the invention, the enzyme product and internal standard are separated from the enzyme reaction mixture. In certain embodiments, buffer salts present in relatively high concentrations in the enzyme reaction mixture are removed by a liquid-liquid extraction step. The extraction step is appropriate for high-throughput analyses to extract the product and internal standard. The presence of a charged carboxylate function on the sugar moiety of IdA-S at, for example, pH 5.4 prevents its extraction into the organic layer, whereas IdA-P and IdA-IS are not charged at pH 5.4 and are readily extracted into ethyl acetate. This extraction step is important as cleavage of the glycosidic bond of IdA-S during ESI-MSMS can occur, forming IdA-P ions and thus giving rise to false-positive IdA activity. The MSMS signal generated by the assay of a normal DBS is generally 4 to 10 times greater than the blank prepared in the conditions mentioned previously.

Thus, in one aspect, the method for assaying α-L-iduronidase enzymatic activity of the invention includes (a) extracting an aqueous enzyme reaction mixture comprising α-L-iduronidase, an α-L-iduronidase product, and an α-L-iduronidase internal standard with an organic solvent to provide an organic phase comprising the α-L-iduronidase product and α-L-iduronidase internal standard; and (b) determining the quantity of the α-L-iduronidase product. As noted above, the quantity of enzyme product is related to the α-L-iduronidase enzymatic activity in a sample that is assayed by the method. In this method, aqueous enzyme reaction mixture comprising α-L-iduronidase, α-L-iduronidase product, and α-L-iduronidase internal standard, and the enzyme is from a sample to be assayed (e.g., a newborn dried blood spot); and the α-L-iduronidase substrate, α-L-iduronidase product, α-L-iduronidase internal standard, organic solvent, and quantification of the product are as described above.

As described above, the addition of the internal standard to the enzyme reaction mixture may occur at different stages in the method. Thus, embodiments of the method of the invention differ in the point at which the internal standard is included.

In one embodiment, the invention provides a method for assaying α-L-iduronidase enzymatic activity that includes (a) incubating an α-L-iduronidase substrate with α-L-iduronidase to provide an enzyme reaction mixture containing an α-L-iduronidase product; (b) quenching the enzyme reaction; (c) adding an α-L-iduronidase internal standard to the enzyme reaction mixture; (d) extracting the enzyme reaction mixture with an organic solvent to provide an organic phase comprising the α-L-iduronidase product and α-L-iduronidase internal standard; and (e) quantifying the α-L-iduronidase product.

In another embodiment, the invention provides a method for assaying α-L-iduronidase enzymatic activity that includes (a) incubating an α-L-iduronidase substrate with α-L-iduronidase to provide an enzyme reaction mixture containing an α-L-iduronidase product; (b) quenching the enzyme reaction with a buffer solution that includes an α-L-iduronidase internal standard; (c) extracting the enzyme reaction mixture with an organic solvent to provide an organic phase comprising the α-L-iduronidase product and α-L-iduronidase internal standard; and (d) quantifying the α-L-iduronidase product.

In another embodiment, the invention provides a method for assaying α-L-iduronidase enzymatic activity that includes (a) incubating an α-L-iduronidase substrate with α-L-iduronidase in the presence of an α-L-iduronidase internal standard to provide an enzyme reaction mixture containing an α-L-iduronidase product; (b) quenching the enzyme reaction; (c) extracting the enzyme reaction mixture with an organic solvent to provide an organic phase comprising the α-L-iduronidase product and α-L-iduronidase internal standard; and (d) quantifying the α-L-iduronidase product.

In these methods, the α-L-iduronidase is from a sample to be assayed (e.g., a newborn dried blood spot); and the α-L-iduronidase substrate, α-L-iduronidase product, α-L-iduronidase internal standard, organic solvent, and quantification of the product are as described above.

Figure 5:
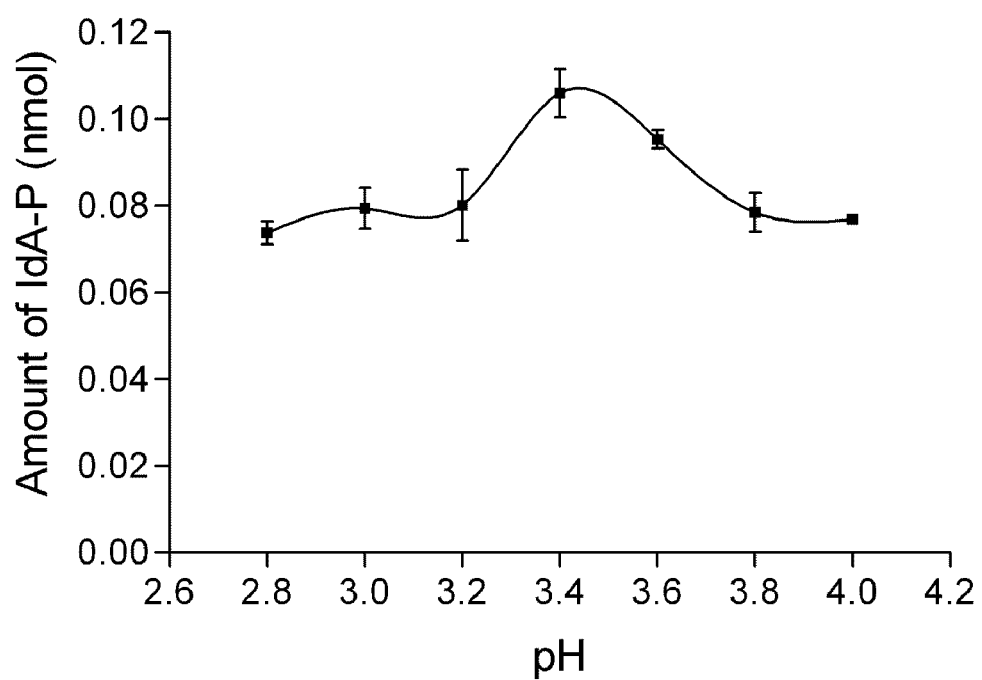
FIG. 5 is a graph illustrating the amount of IdA-generated product measured in dried blood spots (DBS) as a function of the pH of the enzymatic reaction during incubation, reactions were carried out at 37° C. for 20 h using the assay described herein (error bars are shown for triplicate analyses)
Figure 6:
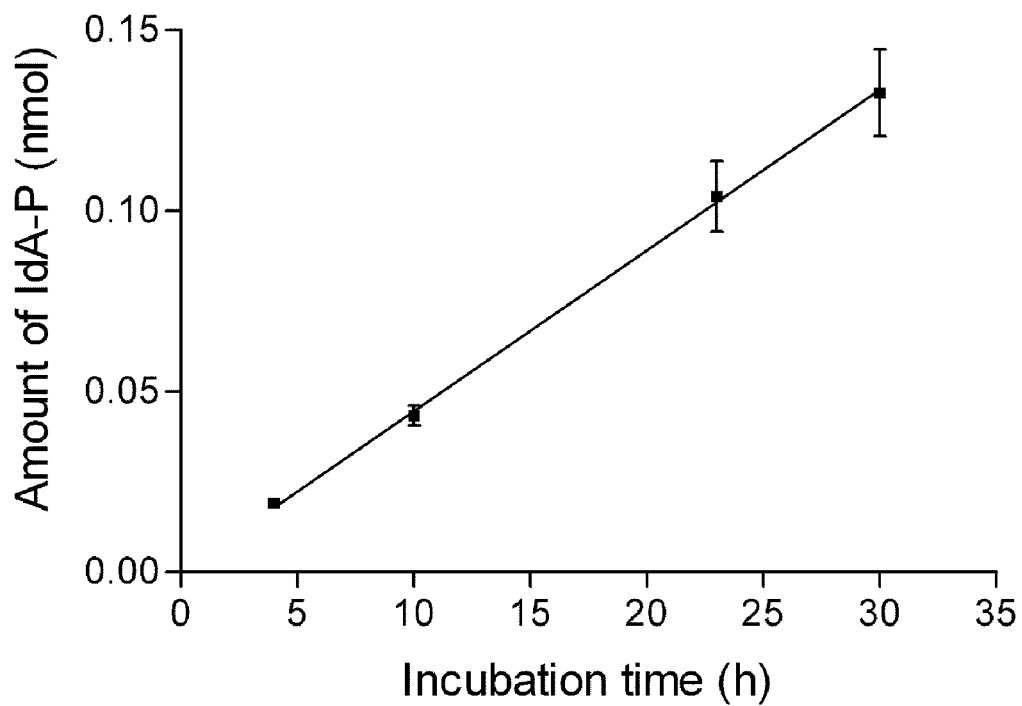
FIG. 6 is a graph illustrating the amount of IdA-generated product (nmol) measured in DBS as a function of incubation time, reactions were carried out at 37° C. using 0.5 mmol/L IdA-S and the conditions described herein (error bars are shown for triplicate analyses; the solid line shows the linear regression fit of the data)
Figure 7:
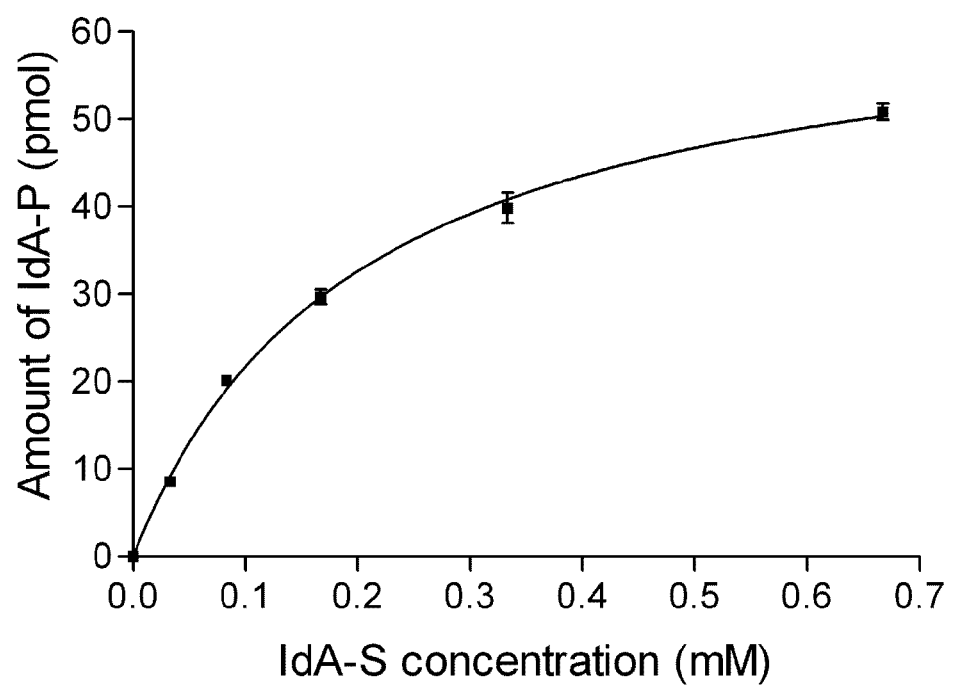
FIG. 7 is a graph illustrating the amount of IdA-generated product (nmol) measured in DBS as a function of the concentration of IdA-S, reactions were carried out at 37° C. for 20 h using the assay described herein (error bars are shown for triplicate analyses; the solid line shows the regression fit of the data to the Michaelis-Menten equation)
Figure 8:
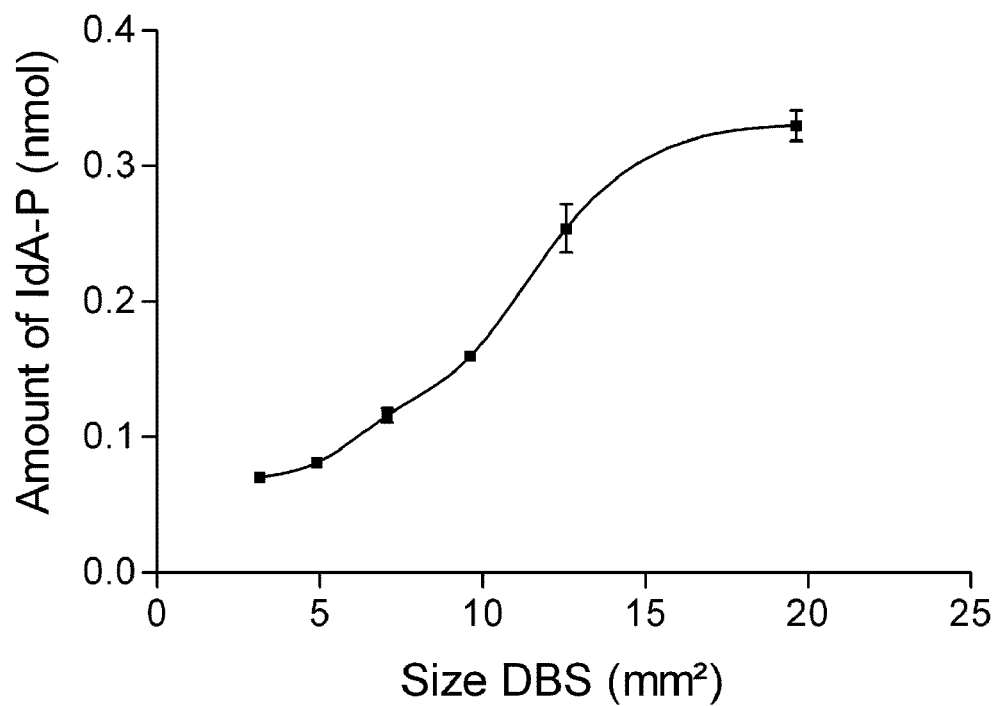
FIG. 8 is a graph illustrating the amount of IdA-generated product (nmol) measured in DBS as a function of the size of the DBS punch, reactions were carried out at 37° C. for 20 h using the assay described herein (error bars are shown for triplicate analyses)

A representative method of the invention for assaying α-L-iduronidase enzymatic activity by tandem mass spectrometry is described in Example 3. Assay optimization showed maximum IdA activity at pH 3.4 (FIG. 5). The amount of IdA-P increases linearly with incubation time from 0 to 30 h (FIG. 6); 20 h was chosen as the standard incubation time for the assay described in Example 3. The amount of IdA-P formed at 20 h increased in a hyperbolic fashion as the concentration of IdA-S increased from 0 to 0.67 mmol/L, and $K_m$ was determined to be 0.2 mmol/L (FIG. 7). An IdA-S concentration of 0.5 mmol/L was chosen in order to be under saturation conditions. The amount of IdA-P increases with the surface area of added DBS (FIG. 8), with a plateau reached at higher blood amounts (presumably due to the presence of endogenous inhibitors in the DBS). In one embodiment, the method uses a 3-mm-DBS punch.

Figure 10:
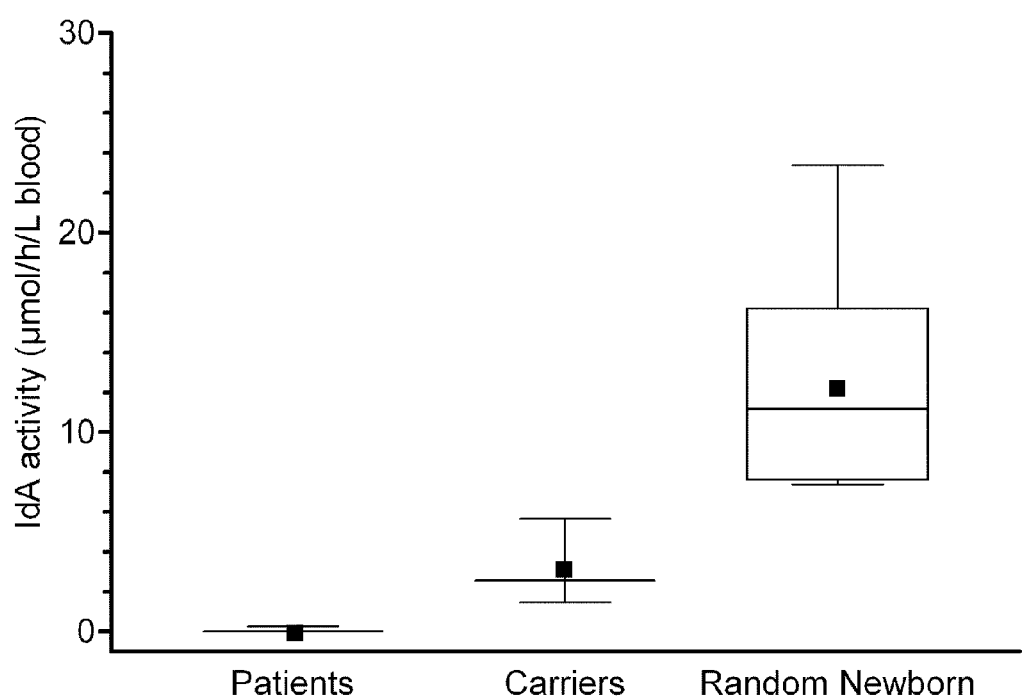
FIG. 10 is graph comparing IdA activities (μmol/h/L blood) determined by the method of the invention for samples obtained from affected newborns (Patients), mucopolysaccharidosis type-1 (MPS-I) carriers (Carriers), and unaffected newborns (Random Newborn)

As shown in FIG. 10, IdA activity in 5 patients (range, 0-0.268; mean, 0.053 μmol/h/L blood) was well below the range of activity in samples obtained from 10 unaffected newborns (random newborns) (range, 7.4-23.4; mean, 12.3 μmol/h/L blood). IdA activity in the 5 MPS-I carriers (carriers) was intermediate (range, 1.4-5.6; mean, 2.9 μmol/h/L blood), but still well separated from the activities from the affected patients. Assay imprecision was calculated by replicate analysis of the DBS from a healthy control: the within-assay CV was 5.9% (n=3), and the interassay CV was 9.3% (n=10).

In another aspect of the invention, a method for assaying α-L-iduronidase enzymatic activity by fluorometry is provided. In one embodiment, the fluorometric method includes a liquid-liquid extraction step (as described above) to separate the α-L-iduronidase product from the enzyme reaction mixture. In another embodiment, the fluorometric method includes a solid phase extraction step (as described above) to separate the α-L-iduronidase product from the enzyme reaction mixture. However, unlike the tandem mass spectrometric method, the fluorometric method does not utilize an internal standard. In the fluorometric method, the enzyme product is isolated by methods described above and quantified using a standard calibration curve. In one embodiment, the fluorometric method utilizes the α-L-iduronidase substrates (i.e., the substrates having formula (I)) to produce the products (i.e., the products having formula (II)) described above. Suitable calibrants include the enzyme product itself, coumarin, and methyl umbelliferone, among others.

Thus, in another embodiment, the invention provides a method for assaying α-L-iduronidase enzymatic activity, comprising:

(a) contacting a dried blood sample with a first buffer solution to provide a solution comprising α-L-iduronidase;

(b) adding an α-L-iduronidase substrate to the solution comprising α-L-iduronidase and incubating the substrate with the enzyme for a pre-determined time to provide a solution comprising an α-L-iduronidase product;

(c) adding a second buffer to quench the enzyme reaction;

(d) separating the α-L-iduronidase product from the enzyme reaction; and (e) measuring the fluorescence intensity of a solution containing the α-L-iduronidase product.

In one embodiment, the fluorometric method includes a liquid-liquid extraction step to separate the α-L-iduronidase product from the enzyme reaction mixture. In another embodiment, the fluorometric method includes a solid phase extraction step to separate the α-L-iduronidase product from the enzyme reaction mixture. It will be appreciated that in this method the substrate can be included in the first buffer.

In a further aspect of the invention, methods for screening newborns for Mucopolysaccharidosis Type-I (MPS-I) are provided. In various embodiments, the MPS-I screening methods of the invention can employ each of the methods described above for assaying α-L-iduronidase enzymatic activity (i.e., each of the embodiments of the assays described above are suitable for the screening methods). In the screening methods, the α-L-iduronidase is obtained from a newborn blood sample (e.g., a dried blood spot) and the amount of α-L-iduronidase product is used to determine whether the blood sample is from a candidate for treatment for (MPS-I).

In one embodiment, the method for screening newborns for MPS-I includes the following steps:

(a) contacting a dried blood sample from a newborn screening card with a first buffer solution to provide a solution comprising α-L-iduronidase;

(b) adding an α-L-iduronidase substrate to the solution comprising α-L-iduronidase and incubating the substrate with the enzyme for a pre-determined time to provide a solution comprising an α-L-iduronidase product;

(c) adding a second buffer to quench the enzyme reaction;

(d) adding an α-L-iduronidase internal standard to the solution comprising the α-L-iduronidase product to provide a solution comprising the α-L-iduronidase product and α-L-iduronidase internal standard;

(e) extracting the solution comprising the α-L-iduronidase product and α-L-iduronidase internal standard with an organic solvent to provide an organic phase that includes the α-L-iduronidase product and α-L-iduronidase internal standard;

(f) determining the quantity of the α-L-iduronidase product by tandem mass spectrometric analysis, comprising (i) generating, isolating, and subjecting the parent ions of the product and internal standard to collision-induced dissociation to provide product fragments ions and internal standard fragment ions, and (ii) comparing the ion peak intensities of the product fragments ions and internal standard fragment ions to calculate the amount of α-L-iduronidase product; and (g) using the amount of α-L-iduronidase product to predict whether the newborn is a candidate for treatment of Mucopolysaccharidosis Type-I.

Representative screening results obtained by the method of the invention described above are presented in Example 3 and illustrated in FIG. 10.

The methods of the invention overcome the deficiencies of a previously developed electrospray ionization tandem mass spectrometry (ESI-MSMS) assay for MPS-I, which used an enzyme substrate obtained from the degradation of commercially available heparin (Wang D, Eadala B, Sadilek M, Chamoles N A, Turecek F, Scott C R, Gelb M H. Tandem mass spectrometric analysis of dried blood spots for screening of Mucopolysaccharidosis I in newborns. Clin Chem 2005; 51:898-900) in which scale-up of the synthesis of the substrate is problematic due to technical difficulties in handling large volumes of nitrous acid for heparin degradation and the necessity of removing impurities from the product. The methods of the present invention provide an improved ESI-MSMS assay that directly measures the reaction velocity of IdA in rehydrated DBS and is adaptable to newborn screening of MPS-I. The method makes use of a modified substrate that can be prepared by total synthesis on a scale suitable for worldwide newborn screening (10 g of substrate for >1 million assays.)

The present invention provides an ESI-MSMS-based assay for IdA that is practical for high-throughput analysis in newborn-screening laboratories and compatible with simultaneous assays of other lysosomal enzymes, including those for which ESI-MSMS-based assays have already been developed. This assay is compatible with microtiter plate and multichannel pipetting techniques (or robotics). The substrate and internal standard used in the assay overcome the synthetic problems encountered previously with the first IdA assay previously developed. Each IdA assay requires only 8.5 μg of substrate and 0.075 μg of internal standard. The pre-ESI-MSMS purification protocol used in the assay is a simple liquid-liquid extraction and is easier to execute than the purification using $C_{18}$-silica plates reported in the previous assay.

The following examples are provide for the purpose of illustrating, not limiting the invention.

EXAMPLES

Example 1

The Synthesis of a Representative Iduronidase Substrate (IdA-S): (N-[4"-(tert-Butoxycarbonylamino)-butyl]) 7-O-(α-L-idopyranosyluronic acid)coumarin-4-acetamide

The synthesis of a representative iduronidase substrate (IdA-S), (N-[4"-(tert-butoxycarbonylamino)-butyl]) 7-O-(α-L-idopyranosyluronic acid)coumarin-4-acetamide described below is a small scale (milligrams amount) synthesis of IdA-S. The synthesis is illustrated schematically in FIG. 3.

Methyl (2,3,4-tri-O-acetyl-(3-D-glucopyranosylfluoride) uronate (2). Methyl 1,2,3,4-tetra-O-acetyl-α,β-D-glucopyranosyluronate 1 (4.98 g, 13.25 mmol, 1 eq) was suspended at 0° C. in 67 mL of 33% hydrobromic acid in acetic acid under nitrogen. After stirring for 15 min at 0° C., the reaction mixture was allowed to warm up to room temperature and stirred for 2 h. The reaction mixture was then diluted with toluene and concentrated under vacuum. The residue was diluted with 250 mL of ethyl acetate and washed with 150 mL of cold saturated sodium bicarbonate and 150 mL of cold brine. The organic layer was dried over $MgSO_4$ and concentrated under vacuum to yield the crude bromide derivative used directly in the next step. The bromide intermediate was dissolved in 167 mL of anhydrous acetonitrile under nitrogen at room temperature. Silver fluoride (3.36 g, 26.49 mmol, 2 eq) was then added. The reaction mixture was stirred for a total of 21 h in the dark. The reaction mixture was filtered through Celite and the filtrate concentrated under vacuum. Column chromatography on silica gel (hexane:EtOAc, 4:1 to 2:1) afforded product 2 (3.3 g, 74%): Spectral data were in good agreement with those reported.

Methyl (5-bromo-2,3,4-tri-O-acetyl-β-D-glucopyranosylfluoride) uronate (3). A suspension of 2 (3.3 g, 9.8 mmol, 1 eq) and N-bromosuccinimide (3.32 g, 18.65 mmol, 1.9 eq) in anhydrous carbon tetrachloride was stirred under nitrogen and under reflux with irradiation for a total of 6 h. N-bromosuccinimide (3.32 g, 18.65 mmol, 1.9 eq) was added after 2 h and 4 h reaction. The reaction mixture was cooled to room temperature and filtered through glass wool. The solvent was removed under vacuum. Column chromatography on silica gel (hexane:EtOAc, 3:1) afforded product 3 (3.12 g, 77%): Spectral data were in good agreement with those reported.

Methyl (2,3,4-tri-O-acetyl-α-L-idopyranosylfluoride) uronate (4). Bromide 3 (3.16 g, 7.61 mmol, 1 eq) was dissolved in 50 mL of anhydrous benzene and stirred under nitrogen. Tributyltin hydride (3.1 mL, 11.4 mmol, 1.5 eq) was added, and the reaction mixture was refluxed for 40 min. The mixture was cooled to room temperature, and the solvent was removed under vacuum. Column chromatography on silica gel (toluene:EtOAc, 8:1 to 6:1) afforded product 4 (1.67 g, 65%): Spectral data were in good agreement with those reported.

(2',2',2'-Trichloroethyl) 7-acetoxycoumarin-4-acetate (6a). To a suspension of 7-acetoxycoumarin-4-acetic acid 5 (945 mg, 3.6 mmol, 1 eq) in 47 mL of anhydrous dichloromethane under nitrogen was added 2,2,2-trichloroethanol (431 µL, 4.5 mmol, 1.25 eq). A solution of N,N'-dicyclohexylcarbodiimide (818 mg, 4 mmol, 1.1 eq) in 10 mL of anhydrous dichloromethane was added. The reaction mixture was stirred for 15 min, after which it was diluted with dichloromethane and filtered. The filtrate was concentrated under vacuum. Column chromatography on silica gel ($CH_2Cl_2$ then $CH_2Cl_2$:EtOAc, 10:1) afforded product 6a (1.37 g, 96%): $R_f$ 0.78 ($CH_2Cl_2$:EtOAc, 5:1); $^1$H NMR (300 MHz, $CDCl_3$): δ 7.61 (d, 1H, $J_{5,6}$ 8.7 Hz, H-5), 7.15 (d, 1H, $J_{6,8}$ 2.1 Hz, H-8), 7.07 (dd, 1H, $J_{6,8}$ 2.3, $J_{5,6}$ 8.7 Hz, H-6), 6.42 (s, 1H, H-3), 4.77 (s, 2H, $CH_2CCl_3$), 3.91 (2 s, 2H, $CH_2CO_2$), 2.33 (s, 3H, OAc); $^{13}$C NMR (75 MHz, $CDCl_3$): δ 168.6, 167.0, 154.5, 153.5, 146.5, 125.5, 118.5, 117.0, 116.5, 110.9, 74.6, 37.7, 21.2; ESI-MS: m/z 393 [M+H]$^+$.

(2',2',2'-Trichloroethyl) 7-hydroxycoumarin-4-acetate (6b). A solution of 6a (1.08 g, 2.74 mmol, 1 eq) in 108 mL of anhydrous tetrahydrofuran was prepared under nitrogen at room temperature. A solution of 2 M ammonia in 2-propanol (6.8 mL, 13.7 mmol, 5 eq) was added dropwise. The reaction mixture was stirred at room temperature in a tightly sealed flask for 18 h. The reaction mixture was concentrated under vacuum. Purification by column chromatography on silica gel ($CH_2Cl_2$, then $CH_2Cl_2$:EtOAc, 10:1 to 5:1) afforded product 6b (753 mg, 78%): $R_f$ 0.6 ($CH_2Cl_2$:EtOAc, 5:1); $^1$H NMR (300 MHz, $d_6$-DMSO): δ 7.55 (d, 1H, $J_{5,6}$ 8.7 Hz, H-5), 6.79 (dd, 1H, $J_{6,8}$ 2.3, $J_{5,6}$ 8.7 Hz, H-6), 6.74 (d, 1H, $J_{6,8}$ 2.3 Hz, H-8), 6.31 (s, 1H, H-3), 4.94 (s, 2H, $CH_2CCl_3$), 4.14 (2 s, 2H, $CH_2CO_2$); $^{13}$C NMR (75 MHz, $d_6$-DMSO): δ 168.4, 161.8, 160.5, 155.5, 149.2, 127.3, 113.5, 112.9, 111.5, 102.8, 95.5, 74.0, 36.9; ESI-MS: m/z 351 [M+H]$^+$.

(2",2",2"-trichloroethyl) 7-O-(methyl 2',3',4'-tri-O-acetyl-α-L-idopyranosyluronate)coumarin-4-acetate (7). A suspension of 6b (703 mg, 2 mmol, 1.26 eq) and $LiClO_4/SiO_2$ (200 mg) in 2 mL of anhydrous dichloromethane was stirred at room temperature under nitrogen. 1,1,1,3,3,3-Hexamethyldisilazane (835 µL, 4 mmol, 2.52 eq) was added dropwise. The reaction mixture was stirred for 35 min. The reaction mixture was diluted with dichloromethane and filtered. The filtrate was concentrated by rotary evaporation to afford (2',2',2'-trichloroethyl) 7-O-trimethylsilylcoumarin-4-acetate 6c, which was used in the next step without further purification. A solution of glycosyl donor 4 (534 mg, 1.6 mmol, 1 eq) and previously prepared glycosyl acceptor 6c in 10 mL of anhydrous dichloromethane under nitrogen was cooled down to 0° C. Boron trifluoride diethyl etherate (196 µL, 1.6 mmol, 1 eq) was added dropwise, after which the reaction mixture was allowed to warm to room temperature. The reaction flask was tightly sealed, and the reaction mixture was stirred for 1.5 h, and then concentrated under vacuum. The residue was dissolved in acetic anhydride (10 mL), and boron trifluoride diethyl etherate (88 µL) was added. After stirring for 20 min, the reaction was diluted with 200 mL of dichloromethane and washed with 100 mL of water, 100 mL of saturated sodium bicarbonate and 100 mL of brine. The organic layer was dried over $MgSO_4$ and concentrated under vacuum with additional co-evaporations with toluene. Column chromatography on silica gel ($CH_2Cl_2$, then $CH_2Cl_2$:EtOAc, 10:1 to 5:1) afforded product 7 (934 mg, 88%): $[α]_D$ −80° (c 1, $CHCl_3$); $R_f$ 0.5 ($CH_2Cl_2$:EtOAc, 5:1); $^1$H NMR (300 MHz, $CDCl_3$): δ 7.53 (d, 1H, $J_{5,6}$ 8.7 Hz, H-5), 7.06 (d, 1H, $J_{6,8}$ 2.5 Hz, H-8), 7.01 (dd, 1H, $J_{6,8}$ 2.5, $J_{5,6}$ 8.9 Hz, H-6), 6.33 (s, 1H, H-3), 5.84 (d, 1H, $J_{1',2'}$ 2.5 Hz, H-1'), 5.20 (m, 2H, H-3', H-4'), 5.05 (m, 1H, H-2'), 4.89 (m, 1H, H-5'), 4.77 (2 s, 2H, $CH_2CCl_3$), 3.87 (s, 2H, $CH_2CO_2$), 3.77 (s, 3H, $CO_2Me$), 2.16-2.09 (3 s, 9H, 3OAc); $^{13}$C NMR (75 MHz, $CDCl_3$) δ 169.5, 169.4, 169.0, 167.9, 167.2, 160.2, 158.9, 155.3, 146.7, 126.0, 115.7, 114.1, 113.2, 104.9, 95.7, 94.5, 74.6, 67.8, 67.0, 66.8, 52.9, 37.7, 20.9, 20.9, 20.7; ESI-MS: m/z 667 [M+H]$^+$.

(N-[4"-(tert-butoxycarbonylamino)-butyl]) 7-O-(methyl 2',3',4'-tri-O-acetyl-α-L-idopyranosyluronate)coumarin-4-acetamide (9a). Glycoside 7 (831 mg, 1.2 mmol, 1 eq) was dissolved in 41 mL of anhydrous tetrahydrofuran at room temperature. The solution was cooled to 0° C., and 90% aqueous acetic acid (5.5 mL) was added. Finally, copper chloride (167 mg, 1.2 mmol, 1 eq) and zinc dust (813 mg, 12.4 mmol, 10 eq) were added. The reaction mixture was stirred at 0° C. for a total of 39 h, during which zinc dust (813 mg, 12.4 mmol, 10 eq) was added after 15 h and 25 h reaction. The reaction mixture was filtered through Celite, and the filtrate was concentrated under vacuum. The residue was solubilized in 200 mL of dichloromethane and washed with 150 mL of water (twice) and 150 mL brine. The organic layer was dried over $MgSO_4$ and concentrated under vacuum. Column chromatography on silica gel ($CH_2Cl_2$, then $CH_2Cl_2$:EtOAc, 5:1 to 2:1; all solvents with 1% acetic acid) afforded product 8 (634 mg, 95%). A solution of acid 8 (627 mg, 1.2 mmol, 1 eq) in 20 mL of anhydrous tetrahydrofuran was cooled to 0° C. N-(3-Dimethylaminopropyl)-N'-ethylcarbodiimide hydrochloride (245 mg, 1.28 mmol, 1.1 eq) and 1-hydroxybenzotriazole (196 mg, 1.28 mmol, 1.1 eq) were added, and the suspension was stirred for 30 min at 0° C. A solution of N-Boc-1,4-diaminobutane (223 µL, 1.2 mmol, 1 eq) in 2 mL of anhydrous N,N-dimethylformamide was slowly added to the suspension. The reaction mixture was allowed to warm to room temperature and stirred for 3 h. The reaction mixture was concentrated under vacuum. The residue was taken up in 250 mL of ethyl acetate and washed with 150 mL of 1 M HCl, 150 mL of water and 150 mL of brine. The organic layer was dried over $MgSO_4$ and concentrated under vacuum. Column chromatography on silica gel (toluene:acetone, 3:1 to 2:1) afforded product 9a (528 mg, 65%): $[α]_D$-70° (c 0.85, $CHCl_3$); $R_f$ 0.38 ($CH_2Cl_2$:MeOH, 95:5); $^1$H NMR (300 MHz, $CDCl_3$): δ 7.67 (d, 1H, $J_{5,6}$ 8.7 Hz, H-5), 7.03 (d, 1H, $J_{6,8}$ 2.3 Hz, H-8), 6.99 (dd, 1H, $J_{6,8}$ 2.5, $J_{5,6}$ 8.7 Hz, H-6), 6.29 (s, 1H, H-3), 5.84 (d, 1H, $J_{1',2'}$ 2.1 Hz, H-1'), 5.20 (m, 2H, H-3', H-4'), 5.04 (m, 1H, H-2'), 4.89 (d, 1H, $J_{4',5'}$ 2.1 Hz, H-5'), 3.77 (s, 3H, $CO_2Me$), 3.65 (s, 2H, $CH_2CONH$), 3.26 (m, 2H, $CH_2NHCO$), 3.09 (m, 2H, $CH_2NHCO$), 2.17-2.09 (3 s, 9H, 3OAc), 1.49 (m, 4H, $CH_2$—$CH_2$), 1.42 (s, 9H, $CMe_3$); $^{13}$C NMR (75 MHz, $CDCl_3$) δ 169.4, 169.4, 169.0, 167.8, 167.6, 160.7, 158.8, 156.4, 155.2, 149.7, 126.7, 114.5, 114.5, 113.2, 104.5, 95.6, 79.4, 67.7, 66.9, 66.6, 52.8, 39.8, 28.5, 20.8, 20.8, 20.6; ESI-MS: m/z 707 [M+H]$^+$.

(N-[4"-(tert-butoxycarbonylamino)-butyl]) 7-O-(α-L-idopyranosyluronic acid)coumarin-4-acetamide (IdA-S). A solution of 9a (98 mg, 0.165 mmol, 1 eq) in 16 mL of methanol was cooled to 0° C. A solution of 0.5 M sodium methoxide in methanol (140 µL, 0.07 mmol, 0.4 eq) was added dropwise. The reaction mixture was stirred at 0° C. for 1.5 h. The reaction mixture was neutralized with Amberlite IR-120 (H$^+$) and filtered. The filtrate was concentrated under vacuum. Column chromatography on silica gel ($CH_2Cl_2$ then $CH_2Cl_2$:MeOH, 9:1) afforded product 9b (69 mg, 86%): $^1$H NMR (300 MHz, $CD_3OD$): δ 7.69 (d, 1H, $J_{5,6}$ 9.7 Hz, H-5), 7.14 (d, 1H, $J_{6,8}$ 2.3 Hz, H-8), 7.13 (dd, 1H, H-6), 6.28 (s, 1H, H-3), 5.76 (d, 1H, $J_{1',2'}$ 3.9 Hz, H-1'), 4.75 (d, 1H, $J_{4',5'}$ 3.5 Hz, H-5'), 3.97-3.89 (m, 2H, H-2', H-3'), 3.77 (s, 3H, $CO_2Me$), 3.74 (s, 2H, $CH_2CONH$), 3.73 (m, 1H, H-4'), 3.21 (m, 2H, $CH_2NHCO$), 3.03 (m, 2H, $CH_2NHCO$), 1.49 (m, 4H, $CH_2$—$CH_2$), 1.42 (s, 9H, $CMe_3$); ESI-MS: m/z 581 [M+H]$^+$. Compound 9b (21 mg, 0.036 mmol, 1 eq) was dissolved in 2 mL of water/methanol (1:1) at room temperature. An aqueous solution of sodium hydroxide 0.1 M was added in increments of 0.1 eq of NaOH until the pH of the solution reached approximately 8 (pH paper). The pH was maintained by incremental additions of the 0.1 M NaOH solution as the reaction proceeded. The reaction mixture was stirred for 5.5 h. The reaction mixture was neutralized with Amberlite IR-120 (H+) and filtered. The filtrate was concentrated under vacuum and then lyophilized to yield product IdA-S (20 mg, quant.): $[\alpha]_D$ −29° (c 0.66, MeOH); $^1$H NMR (300 MHz, CD$_3$OD): δ 7.68 (d, 1H, $J_{5,6}$ 8.9 Hz, H-5), 7.54 (dd, 1H, $J_{6,8}$ 2.5, $J_{5,6}$ 8.9 Hz, H-6), 7.46 (d, 1H, $J_{6,8}$ 2.3 Hz, H-8), 6.25 (s, 1H, H-3), 5.58 (d, 1H, $J_{1',2'}$ 6.8 Hz, H-1'), 4.36 (d, 1H, $J_{4',5'}$ 5.6 Hz, H-5'), 3.73 (s, 2H, CH$_2$CONH), 3.69-3.48 (m, 3H, H-2', H-3', H-4'), 3.21 (m, 2H, CH$_2$NHCO), 3.03 (m, 2H, CH$_2$NHCO), 1.49 (m, 4H, CH$_2$—CH$_2$), 1.42 (s, 9H, CMe$_3$); ESI-MS: m/z 567 [M+H]+.

Example 2

The Synthesis of a Representative Iduronidase Internal Standard (IdA-IS): (N-[3'-(tert-butoxycarbonylamino)-propyl]) 7-hydroxycoumarin-4-acetamide The synthesis of a representative iduronidase internal standard (IdA-IS), (N-[3'-(tert-butoxycarbonylamino)-propyl]) 7-hydroxycoumarin-4-acetamide, described below is a small scale (milligrams amount) synthesis of IdA-IS. The synthesis is illustrated schematically in FIG. 4.

(N-[3'-(tert-butoxycarbonylamino)-propyl]) 7-acetoxycoumarin-4-acetamide (10). A solution of 5 (302 mg, 1.15 mmol, 1 eq) in 20 mL of anhydrous tetrahydrofuran was cooled to 0° C. N-(3-Dimethylaminopropyl)-N'-ethylcarbodiimide hydrochloride (243 mg, 1.27 mmol, 1.1 eq) and 1-hydroxybenzotriazole (194 mg, 1.27 mmol, 1.1 eq) were added, and the suspension was stirred for 30 min at 0° C. A solution of N-Boc-1,3-diaminopropane (201 µL, 1.15 mmol, 1 eq) in 1 mL of anhydrous N,N-dimethylformamide was slowly added to the suspension. The reaction mixture was allowed to warm to room temperature and stirred for 6 h. The reaction mixture was concentrated under vacuum. The residue was taken up in 200 mL of ethyl acetate and washed with 60 mL of 1 M HCl, 60 mL of water and 60 mL of brine. The organic layer was dried over MgSO$_4$ and concentrated under vacuum. Column chromatography on silica gel (CH$_2$Cl$_2$, then CH$_2$Cl$_2$:MeOH, 98:2 to 97:3) afforded product 10 (296 mg, 61%): $R_f$ 0.6 (CH$_2$Cl$_2$:MeOH, 95:5); $^1$H NMR (300 MHz, CD$_3$OD): δ 7.78 (d, 1H, $J_{5,6}$ 8.7 Hz, H-5), 7.21 (d, 1H, $J_{6,8}$ 2.3 Hz, H-8), 7.15 (dd, 1H, $J_{6,8}$ 2.3, $J_{5,6}$ 8.7 Hz, H-6), 6.41 (s, 1H, H-3), 3.79 (s, 2H, CH$_2$CONH), 3.22 (t, 2H, J=6.8 Hz, CH$_2$NHCO), 3.02 (t, 2H, J=6.8 Hz, CH$_2$NHCO), 2.31 (s, 3H, OAc), 1.63 (m, 2H, CH$_2$—CH$_2$—CH$_2$), 1.41 (s, 9H, CMe$_3$); $^{13}$C NMR (75 MHz, d$_6$-DMSO): δ 168.7, 167.3, 159.5, 152.8, 150.5, 126.4, 118.4, 116.9, 115.5, 110.2, 77.4, 38.8, 37.5, 36.5, 29.4, 28.2, 20.8; ESI-MS: m/z 419 [M+H]+.

(N-[3'-(tert-butoxycarbonylamino)-propyl]) 7-hydroxycoumarin-4-acetamide (IdA-IS). Compound 10 (160 mg, 0.38 mmol, 1 eq) was dissolved in 21 mL of methanol/dichloromethane (6:1), and the solution was cooled to 0° C. A solution of 0.5 M sodium methoxide in methanol (383 µL, 0.19 mmol, 0.5 eq) was added dropwise. After stirring for 30 min at 0° C., the reaction mixture was allowed to warm to room temperature and stirred for 18 h. The reaction mixture was then neutralized with Amberlite IR-120 (H+) and filtered. The filtrate was concentrated under vacuum. Purification by column chromatography on silica gel (CH$_2$Cl$_2$, then CH$_2$Cl$_2$:MeOH, 95:5 to 90:10) afforded product IdA-IS (132 mg, 92%): $R_f$ 0.24 (CH$_2$Cl$_2$:MeOH, 95:5); $^1$H NMR (300 MHz, d$_6$-DMSO): δ 10.57 (bs, 1H, OH), 8.17 (t, 1H, J=5.4 Hz, NH), 7.62 (d, 1H, $J_{5,6}$ 8.7 Hz, H-5), 6.82 (dd, 1H, $J_{6,8}$ 2.3, $J_{5,6}$ 8.7 Hz, H-6), 6.79 (m, 1H, NH), 6.75 (d, 1H, $J_{6,8}$ 2.5 Hz, H-8), 6.19 (s, 1H, H-3), 3.66 (s, 2H, CH$_2$CONH), 3.08 (m, 2H, CH$_2$NHCO), 2.94 (m, 2H, CH$_2$NHCO), 1.54 (m, 2H, CH$_2$—CH$_2$—CH$_2$), 1.40 (s, 9H, CMe$_3$); $^{13}$C NMR (75 MHz, d$_6$-DMSO): δ 167.5, 161.1, 160.2, 155.0, 151.1, 126.6, 112.9, 111.8, 111.5, 102.3, 77.5, 37.5, 36.6, 29.5, 28.2; ESI-MS: m/z 377 [M+H]+.

Example 3

Representative ESI-MSMS Method for Directly Assaying α-L-Iduronidase Enzymatic Activity In this example, a representative method of the invention (tandem mass spectrometry) for directly assaying α-L-uronidase enzymatic activity from dried blood spots (DBS) from a newborn screening card is described.

All experiments were conducted in compliance with Institutional Review Board guidelines. All MPS-I affected patients had been diagnosed previously with established clinical and biochemical procedures. DBS were kept at ambient temperature during shipment (<10 days) and then stored at −20° C. in zip-lock plastic bags (one bag sealed inside a second bag). Zip-lock bags were kept in a sealed plastic box containing desiccant (anhydrous CaSO$_4$ granules).

A single 3-mm diameter DBS (containing ~3.6 µL of blood) was obtained with a leather punch and was placed in a 1-mL Eppendorf tube. Extraction buffer [160 µL of 0.1 mol/L sodium formate pH 3.4 containing 75 µmol/L D-saccharic acid 1,4-lactone (Sigma); storage at −20° C.] was added to the tube. After vortex-mixing for 1 min, the tube was rocked gently on an orbital shaker for 45 min at 37° C. Twenty microliters of this blood extract was transferred to a 0.6-mL Eppendorf tube, and 10 µL of 1.5 mmol/L IdA-S in water (stored at −20° C.) was added. The enzymatic reaction was incubated for 20 hours at 37° C. in a thermostated-air shaker and then was quenched by adding 100 µL of 0.1 mol/L sodium acetate pH 5.4. Ten microliters of 20 µmol/L IdA-IS in water (stored at −20° C.) was also added, and the tube was vortex-mixed. A blank was prepared by incubating a tube with 20 µL of blood extract and a tube with 10 µL of 1.5 mmol/L IdA-S in 0.1 mol/L sodium formate pH 3.4 separately at 37° C. for 20 hours, followed by mixing the two solutions together and adding 100 µL of 0.1 mol/L sodium acetate pH 5.4 and 10 µL of 20 µmol/L IdA-IS in water.

Extraction of IdA-P and IdA-IS from the enzymatic reaction and blank was performed by addition of 250 µL of ethyl acetate. After vortex-mixing for 15 s, the tube was centrifuged for 1 min using a table-top centrifuge at maximum speed. A 200 µL aliquot of the top organic layer was transferred to a 1-mL Eppendorf tube. The solvent was removed under a stream of nitrogen (typically 30 min at room temperature). To the residue was added 70 µL of 5 mmol/L ammonium formate in methanol, and the sample was transferred into a well of a 96-well plate (Greiner Bio-One, cat. #651201) for the Waters sample manager. The sample (20 µL of the 70 µL sample in 5 mmol/L ammonium formate in methanol) was injected into the mass spectrometer with a Waters autoinjector system. After sample injection, 0.2% formic acid in methanol was infused for 4 min at 0.2 mL/min to deliver the sample to the mass spectrometer and clean the delivery line prior to the next injection. MSMS data was collected in the period 0-3 min after sample injection. The sample was analyzed within the first 45 seconds of infusion, and after 1 min, the MSMS signal has returned to the background level. In newborn screening laboratories, the analysis could be reduced to 1-2 min per sample to minimize the time spent on a given sample.

ESI-MSMS was carried out on a Waters ACQUITY tandem quadrupole instrument operating in positive-ion, multiple-reaction monitoring mode. Ion scanning was carried out with MassLynx 4.1 software with the following settings: capillary voltage, 4500 V; cone voltage, 19 V; extractor, 3 V; RF, 0.4 V; source temperature, 80° C.; desolvation temperature, 250° C.; cone gas flow, 0 L/h; desolvation gas flow, 500 L/h; collision gas flow, 0.20 mL/min; LM 1 resolution, 13.2; HM 1 resolution, 14.6; ion energy 1, 0; MSMS mode entrance, 1; MSMS collision energy, 10 eV (IdA-P) and 9 eV (IdA-IS); MSMS mode exit, 0.5; LM 2 resolution, 13.0; HM 2 resolution, 14.6; ion energy 2, 0.7; collision cell pressure, ~3.7e-3 mbar; collision gas, argon. Multiple-reaction-monitoring mode was used for m/z 391.2→291.1 and 377.2→277.1 transitions with the following settings: dwell time, 0.1 s; delay, 0.02 s.

Figure 9:
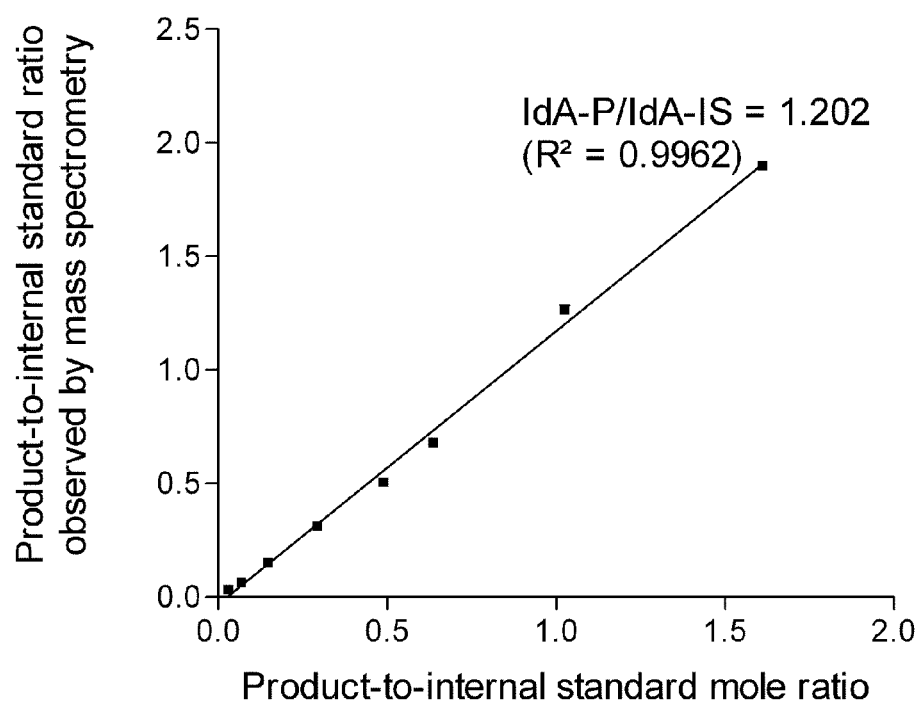
FIG. 9 is a graph illustrating the product-to-internal standard (IdA-P/IdA-IS) ion ratio observed by ESI-MSMS as a function of the relative amount of IdA-P and IdA-IS added to the IdA assay (product-to-internal standard ratio), samples contained all assay components except substrate, a fixed amount of IdA-IS (0.2 nmol) and various amounts of IdA-P (error bars are shown for triplicate analyses; the solid line shows the linear regression fit of the data)

The parent ions for IdA-P and IdA-IS (m/z 391.2 and 377.2, respectively) were isolated and subjected to collision-induced dissociation. The fragment ions analyzed are m/z 291.1 and 277.1 derived from IdA-P and IdA-IS respectively, by elimination of isobutene and carbon dioxide. The amount of product was calculated from the ion abundance ratio of product (IdA-P) to internal standard (IdA-IS), minus that from a blank control (blood extract and substrate in buffer pH 3.4 incubated separately), multiplied by the amount of added internal standard and divided by the response factor ratio of product to internal standard (see FIG. 9). Enzymatic activity was calculated from the amount of product which was divided by the incubation time and the volume of blood (3.6 μL of blood in a 3-mm DBS punch).

In accordance with the method of the invention described in detail above, IdA activities in DBS were measured for MPS-I patients (5), MPS-I carriers (5), and normal newborns (10). The α-L-iduronidase activity measured for 5 patients (MPS-I affected newborns) was well below the interval found for 10 randomly chosen newborns; the activity measured for 5 MPS-I carriers was intermediate that of the affected newborns and randomly chosen newborns. The results are summarized below in Table 1.

TABLE 1

| IdA activities for individual DBS. IdA activity (μmol/h/L blood) | | | |
|---|---|---|---|
| MPS-I patients | MPS-I carriers | Normal newborns | |
| −0.05 | 5.66 | 14.4 | 11.5 |
| −0.15 | 2.55 | 11.2 | 11.1 |
| −0.04 | 2.35 | 23.4 | 18.0 |
| 0.268 | 1.45 | 7.8 | 7.4 |
| −0.67 | 2.60 | 7.4 | 10.6 |

The blank value [mean (SD), 2.67 (0.26) μmol/h/L blood; calculated from 15 independent assays], obtained from an identical assay in which the blood extract and the substrate in buffer pH 3.4 were incubated separately, was subtracted to give the values.

The results are presented graphically in FIG. 10. Referring to FIG. 10, IdA activities are shown with the horizontal bars indicating the full range of values, the box indicating the 25-75% values, where the horizontal line inside the box indicates the median and ■ indicates the mean.

Example 4

Representative Fluorometric Method for Directly Assaying α-L-Iduronidase Enzymatic Activity In this example, a representative method of the invention (fluorometric) for directly assaying α-L-uronidase enzymatic activity from dried blood spots (DBS) is described. The enzyme substrate (IdA-S) used was as described above in Example 1.

Dried blood spots on a filter paper card were used as the enzyme source. The blood extract was prepared as follows: a 3-mm dried blood spot punch (containing ~3.6 μL of blood) was obtained by use of a standard leather punch and placed in a 1 mL Eppendorf tube. Extraction buffer [160 μL of 0.1 M sodium formate pH 3.4 containing 75 μM D-saccharic acid 1,4-lactone] was added to the tube. After vortex-mixing for 1 min, the tube was shaken gently on an orbital shaker for 45 min at 37° C., to give a blood extract containing the enzyme α-L-iduronidase.

Figure 11:
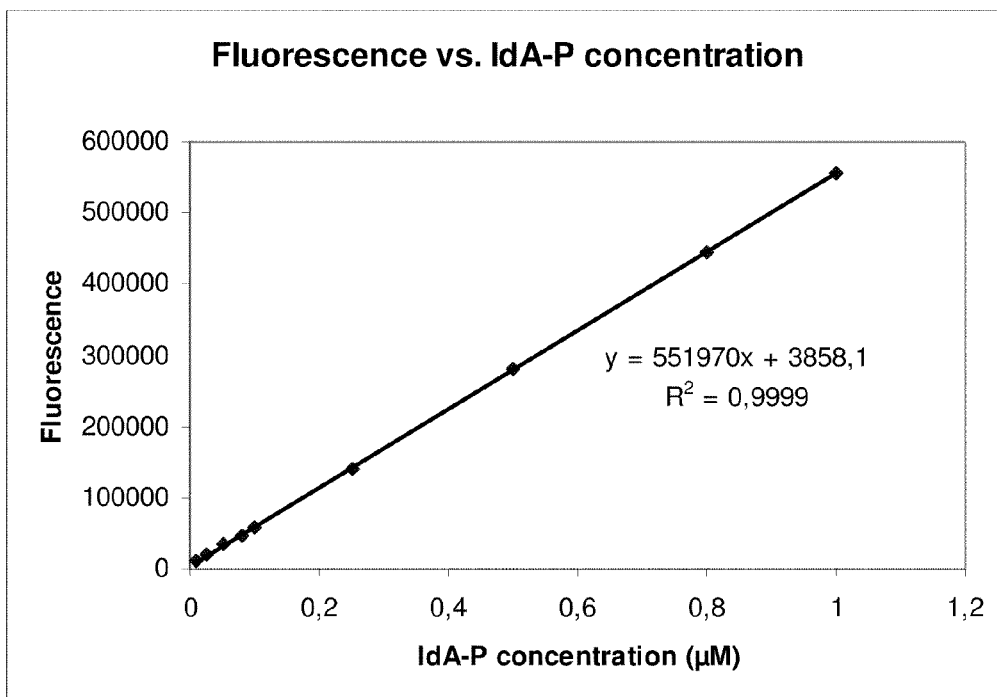
FIG. 11 is a calibration curve showing fluorescence intensity as a function of enzyme product (IdA-P) concentration for a representative fluorometric assay of the invention.

To 20 μL of blood extract was added 10 μL of 1 mM substrate IdA-S in water. After 20 h incubation at 37° C. in a thermostated-air shaker, the reaction was stopped by addition of 100 μL of 85 mM glycine-carbonate pH 10.5, and the fluorescence of the resulting solution was measured. A blank was prepared by incubating a tube with 20 μL of blood extract and a tube with 10 μL of 1 mM substrate IdA-S in 0.1 M sodium formate pH 3.4 separately at 37° C. for 20 h, followed by mixing the two solutions together and adding 100 μL of 85 mM glycine-carbonate pH 10.5. Each assay was done in triplicate, and corrected by subtracting the blank value. The fluorescence measurements of the released aglycone were carried out at the wavelengths $\lambda_{ex}/\lambda_{em}$ 355/460 nm for (N-[4'-(tert-butoxycarbonylamino)-butyl]) 7-hydroxycoumarin-4-acetamide IdA-P on a PerkinElmer fluorometer VICTOR$^3$ V. Using a calibration curve (FIG. 11), enzyme activities were calculated as micromoles of substrate hydrolyzed per hour per liter of blood.

In accordance with the method of the invention described in detail above, IdA activities in DBS were measured for two unaffected individuals. The results are summarized below in Table 2.

TABLE 2

| IdA activities for two unaffected patients. IdA activity (μmol/h/L blood) |
|---|
| Unaffected patients |
| 4.47 |
| 7.17 |

The blank value [mean (SD), 1.83 (0.09) μmol/h/L blood; calculated from 2 independent assays], obtained from an identical assay in which the blood extract and the substrate in buffer pH 3.4 were incubated separately (see main text), was subtracted to give the values.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for assaying α-L-iduronidase enzymatic activity, comprising:
   (a) incubating an α-L-iduronidase substrate which has the formula:

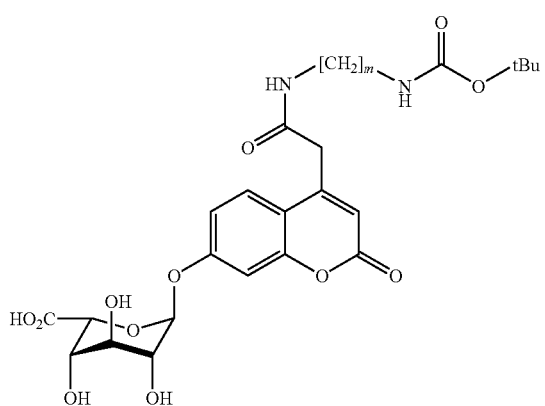

Wherein m is an integer from 2 to 12,
with α-L-iduronidase for a pre-determined time to provide a solution comprising an α-L-iduronidase product;
(b) adding a buffer to the solution comprising the α-L-iduronidase product to quench the enzyme reaction;
(c) adding an α-L-iduronidase internal standard to the solution comprising the α-L-iduronidase product to provide a solution comprising the α-L-iduronidase product and α-L-iduronidase internal standard;
(d) extracting the solution comprising the α-L-iduronidase product and α-L-iduronidase internal standard with an organic solvent to provide an organic phase that includes the α-L-iduronidase product and α-L-iduronidase internal standard; and
(e) determining the quantity of the α-L-iduronidase product.

2. The method of claim 1, wherein the solution comprising α-L-iduronidase is obtained by contacting a sample containing α-L-iduronidase with a first buffer solution.

3. The method of claim 2, wherein the sample is a blood sample.

4. The method of claim 2, wherein the sample is a dried blood spot from a newborn screening card.

5. The method of claim 1, wherein the substrate has a structure wherein m is 4.

6. The method of claim 1, wherein the internal standard has the formula:

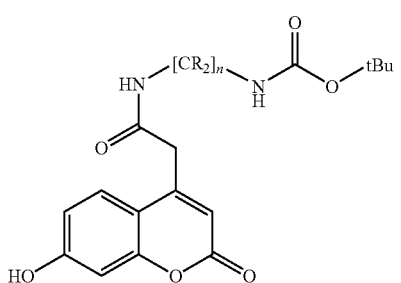

wherein R is independently at each occurrence H or D and n is an integer from 2 to 12.

7. The method of claim 1, wherein the internal standard is (N-[3'-(tert-butoxycarbonylamino)-propyl]) 7-hydroxycoumarin-4-acetamide.

8. The method of claim 1, wherein determining the quantity of the α-L-iduronidase product comprises determining the ratio of the α-L-iduronidase product to α-L-iduronidase internal standard comprises mass spectrometric analysis.

9. The method of claim 1, wherein determining the quantity of the α-L-iduronidase product comprises tandem mass spectrometric analysis.

10. The method of claim 1, wherein determining the quantity of the α-L-iduronidase product comprises tandem mass spectrometric analysis in which the parent ions of the product and internal standard are generated, isolated, and subjected to collision-induced dissociation to provide product fragment ions and internal standard fragment ions.

11. The method of claim 10, wherein determining the quantity of the α-L-iduronidase product comprises comparing the peak intensities of the product fragment ions and internal standard fragment ions to calculate the amount of α-L-iduronidase product.

12. The method of claim 4 further comprising using the amount of α-L-iduronidase product to determine whether the dried blood sample is from a candidate for treatment for Mucopolysaccharidosis Type-I.

13. A method for screening newborns for Mucopolysaccharidosis Type-I, comprising:
(a) contacting a dried blood sample from a newborn screening card with a first buffer solution to provide a solution comprising α-L-iduronidase;
(b) adding an α-L-iduronidase substrate which has the formula:

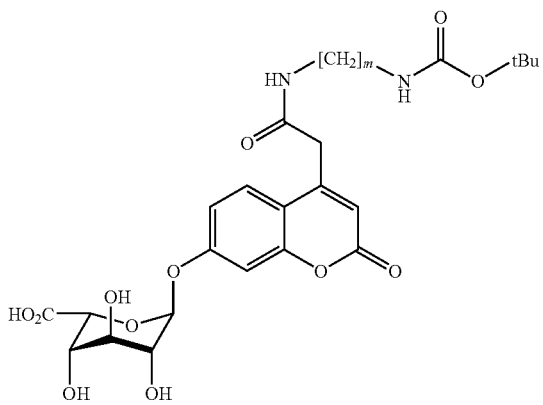

Wherein m is an integer from 2 to 12,
to the solution comprising α-L-iduronidase and incubating the substrate with the enzyme for a pre-determined time to provide a solution comprising an α-L-iduronidase product;
(c) adding a second buffer to the solution comprising the α-L-iduronidase product to quench the enzyme reaction;
(d) adding an α-L-iduronidase internal standard to the solution comprising the α-L-iduronidase product to provide a solution comprising the α-L-iduronidase product and α-L-iduronidase internal standard;
(e) extracting the solution comprising the α-L-iduronidase product and α-L-iduronidase internal standard with an organic solvent to provide an organic phase that includes the α-L-iduronidase product and α-L-iduronidase internal standard;
(f) determining the quantity of the α-L-iduronidase product by tandem mass spectrometric analysis, comprising
(i) generating, isolating, and subjecting the parent ions of the product and internal standard to collision-induced dissociation to provide product fragment ions and internal standard fragment ions, and (ii) comparing the ion peak intensities of the product fragment ions and internal standard fragment ions to calculate the amount of α-L-iduronidase product; and (g) using the amount of α-L-iduronidase product to predict whether the newborn is a candidate for treatment of Mucopolysaccharidosis Type-I.

14. A compound having the formula:

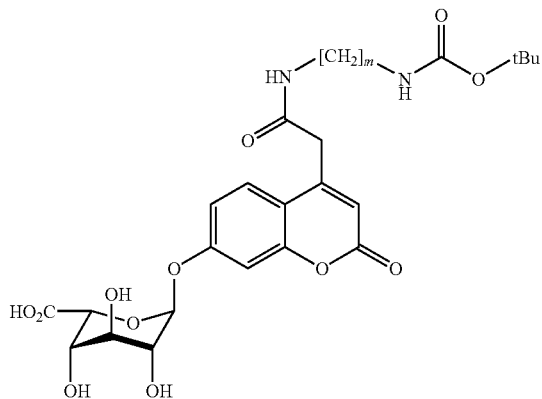

wherein m is an integer from 2 to 12.

15. A compound of claim 14, wherein m is 4.

16. A method for assaying α-L-iduronidase enzymatic activity, comprising:

(a) contacting a dried blood sample with a first buffer solution to provide a solution comprising α-L-iduronidase;

(b) adding an α-L-iduronidase substrate which has the formula:

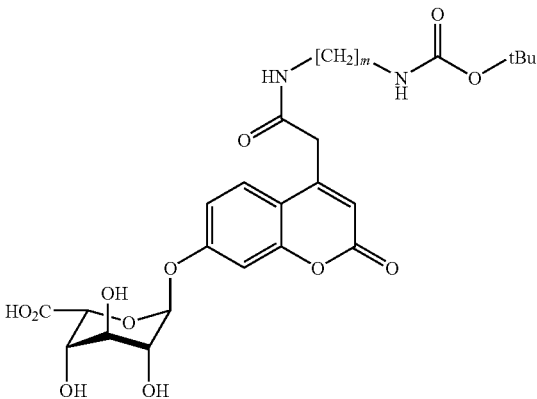

Wherein m is an integer from 2 to 12,
to the solution comprising α-L-iduronidase and incubating the substrate with the enzyme for a pre-determined time to provide a solution comprising an α-L-iduronidase product;

(c) adding a second buffer to the solution comprising the α-L-iduronidase product to quench the enzyme reaction;

(d) separating the α-L-iduronidase product from the enzyme reaction; and (e) measuring the fluorescence intensity of a solution containing the α-L-iduronidase product.

* * * * *